United States Patent [19]
Lawlor

[11] Patent Number: 5,753,479
[45] Date of Patent: May 19, 1998

[54] PHENYLALANYL TRNA SYNTHETASE POLYNUCLEOTIDES OF STREPTOCOCCUS

[75] Inventor: Elizabeth Jane Lawlor, Malvern, Pa.

[73] Assignee: SmithKline Beecham Corporation, Phila., Pa.

[21] Appl. No.: 843,521

[22] Filed: Apr. 18, 1997

[30] Foreign Application Priority Data

Apr. 18, 1996 [GB] United Kingdom ............... 9607993

[51] Int. Cl.$^6$ ............... C12N 9/00; C12N 1/20; C12N 15/00; C07H 21/04
[52] U.S. Cl. ............... 435/183; 435/6; 435/320.1; 435/252.3; 435/254.11; 435/325; 536/23.2; 536/23.4
[58] Field of Search ............... 435/6, 183, 320.1, 435/252.3, 254.11, 325; 536/23.2, 23.4

[56] References Cited

PUBLICATIONS

R. Calendar et al., "Purification and Physical Characterization of Tyrosyl Ribonucleic Acid Synthetases form *Escerichia coli and Bacillus subtilis*", *Biochemistry*, 5(5) pp. 1681–1690 (1966).

J. Hughes et al., "How Does *Pseudomonas Fluorescens*, the Producing Organism of the Antibiotic Pseudomonic Acid A, Avoid Suicide?", *FEBS Letters*, 122(2) pp. 322–324 (1980).

Brakhage et al., "Structure and Nucleotide Sequence of the *Bacillus subtilis* Phenylalanyl–tRNA Synthetase Genes," *Biochime*, 72 pp. 725–734 (1990).

Kreutzer R. et al., "Structure of the Phenylalanyl–tRNA Synthetase Genes from Thermus thermophilus HB8 and Their Expression in E. coli," *Nucleic Acids Research*, 20(1) pp. 4173–4178 (1992).

Fleischmann et al. (1995) Whole–Genome Random Sequencing and Assembly of *Haemophilus influenza* Rd. Science 269:496–512.

*Primary Examiner*—Robert A. Wax
*Assistant Examiner*—Lisa J. Hobbs
*Attorney, Agent, or Firm*—Edward R. Gimmi; William T. King; Edward T. Lentz

[57] ABSTRACT

The invention provides pheS (beta) and pheS (alpha) polypeptides and DNA (RNA) encoding pheS (beta) and pheS (alpha) polypetides and methods for producing such polypeptides by recombinant techniques. Also provided are methods for utilizing pheS (beta) and pheS (alpha) polypeptides to screen for antibacterial compounds.

53 Claims, No Drawings

PHENYLALANYL TRNA SYNTHETASE POLYNUCLEOTIDES OF STREPTOCOCCUS

RELATED APPLICATIONS

This application claims benefit of UK application number 9607993.4, filed Apr. 18, 1996.

FIELD OF THE INVENTION

This invention relates to newly identified polynucleotides and polypeptides, and their production and uses, as well as their variants, agonists and antagonists, and their uses. In particular, in these and in other regards, the invention relates to novel polynucleotides and polypeptides of the phenylalanyl tRNA synthetase (beta sub-unit) family, hereinafter referred to as "pheS (beta)," and the phenylalanyl tRNA synthetase (alpha sub-unit) family, hereinafter referred to as "pheS (alpha)".

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with S. pneumoniae, many questions concerning the virulence of this microbe remain. It is particularly preferred to employ Streptococcal genes and gene products as targets for the development of antibiotics.

The frequency of *Streptococcus pneumoniae* infections has risen dramatically in the past 20 years. This has been attributed to the emergence of multiply antibiotic resistant strains and an increasing population of people with weakened immune systems. It is no longer uncommon to isolate *Streptococcus pneumoniae* strains which are resistant to some or all of the standard antibiotics. This has created a demand for both new anti-microbial agents and diagnostic tests for this organism.

The t-RNA synthetases have a primary role in protein synthesis according to the following scheme:

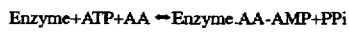

in which AA is an amino acid.

Inhibition of this process leads to a reduction in the levels of charged t-RNA and this triggers a cascade of responses known as the stringent response, the result of which is the induction of a state of dormancy in the organism. As such selective inhibitors of bacterial t-RNA synthetase have potential as antibacterial agents. One example of such is mupirocin which is a selective inhibitor of isoleucyl t-RNA synthetase. Other t-RNA synthetases are now being examined as possible anti-bacterial targets, this process being greatly assisted by the isolation of the synthetase.

Clearly, there is a need for factors, such as the novel compounds of the invention, that have a present benefit of being useful to screen compounds for antibiotic activity. Such factors are also useful to determine their role in pathogenesis of infection, dysfunction and disease. There is also a need for identification and characterization of such factors and their antagonists and agonists which can play a role in preventing, ameliorating or correcting infections, dysfunctions or diseases.

The polypeptides of the invention have amino acid sequence homology to a known *Bacillus subtilis* phenylalanyl tRNA synthetase beta sub-unit protein and *Bacillus subtilis* phenylalanyl tRNA synthetase (alpha sub-unit) protein.

SUMMARY OF THE INVENTION

It is an object of the invention to provide polypeptides that have been identified as novel pheS (beta) and pheS (alpha) polypeptides by homology between the amino acid sequence set out in Table 1 [SEQ ID NO:2, 6 respectively] and a known amino acid sequence or sequences of other proteins such as *Bacillus subtilis* phenylalanyl tRNA synthetase alpha or beta sub-unit protein.

It is a further object of the invention to provide polynucleotides that encode pheS (beta) or pheS (alpha) polypeptides, particularly polynucleotides that encode the polypeptide herein designated pheS (beta) and pheS (alpha).

In a particularly preferred embodiment of the invention the polynucleotide comprises a region encoding pheS (beta) polypeptides comprising the sequence set out in Table 1 [SEQ ID NO:1, 5], or a variant thereof.

In another particularly preferred embodiment of the invention there is a novel pheS (beta) protein from *Streptococcus pneumoniae* comprising the amino acid sequence of Table 1 [SEQ ID NO:2], or a variant thereof.

In another particularly preferred embodiment of the invention there is a novel pheS (alpha) protein from *Streptococcus pneumoniae* comprising the amino acid sequence of Table 1 [SEQ ID NO:6], or a variant thereof.

In accordance with another aspect of the invention there is provided an isolated nucleic acid molecule encoding a mature pheS (alpha) and pheS (beta) polypeptide expressible by the *Streptococcus pneumoniae* 0100993 strain contained in the deposited strain.

A further aspect of the invention there are provided isolated nucleic acid molecules encoding pheS (beta) and/or pheS (alpha), particularly *Streptococcus pneumoniae* pheS (alpha) and/or pheS (beta), including mRNAs, cDNAs, genomic DNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of pheS (beta) and pheS (alpha) and polypeptides encoded thereby.

Another aspect of the invention there are provided novel polypeptides of *Streptococcus pneumoniae* referred to herein as pheS (beta) or pheS (alpha) as well as biologically, diagnostically, prophylactically, clinically or therapeutically useful variants of either polypeptide, and compositions comprising the same.

Among the particularly preferred embodiments of the invention are variants of pheS (beta) or pheS (alpha) polypeptide encoded by naturally occurring alleles of the pheS (beta) or pheS (alpha) gene, respectivley.

In a preferred embodiment of the invention there are provided methods for producing the aforementioned pheS (beta) and pheS (alpha) polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing pheS (beta) and/or pheS (alpha) expression, treating disease, for example, otitis media, conjunctivitis, pneumonia, bacteremia, meningitis, sinusitis, pleural empyema and endocarditis, and most particularly meningitis, such as for example infection of cerebrospinal fluid, assaying genetic variation, and administering a pheS (beta) polypeptide or polynucleotide to an organism to raise an immunological response against a bacteria, especially a *Streptococcus pneumoniae* bacteria.

In accordance with certain preferred embodiments of this and other aspects of the invention there are provided polynucleotides that hybridize to pheS (beta) and/or pheS (alpha) polynucleotide sequences, particularly under stringent conditions.

In certain preferred embodiments of the invention there are provided antibodies against pheS (beta) and/or pheS (alpha) polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypetide or polynucleotide by detecting the presence or absence of a signal generated from the binding or interaction of the compound with the polypeptide or polynucleotide.

In accordance with yet another aspect of the invention, there are provided pheS (beta) and/or pheS (alpha) agonists and antagonists, preferably bacteriostatic or bacteriocidal agonists and antagonists.

In a further aspect of the invention there are provided compositions comprising a pheS (beta) polynucleotide or a pheS (beta) polypeptide for administration to a cell or to a multicellular organism.

In a further aspect of the invention there are provided compositions comprising a pheS (alpha) polynucleotide or a pheS (alpha) polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A.M., ed., Oxford University Press, New York, 1988; *Biocomputing: Informatics and Genome Projects*, Smith, D.W., ed., Academic Press, New York, 1993; *Computer Analysis of Sequence Data*, Part I, Griffin, A.M., and Griffin, H.G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991 and Carillo, H., and Lipman, D., SIAM J. *Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S.F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously , by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins, and further includes homo- and hethero-dimers, trimers and tetramers of pheS (beta) and/or pheS (alpha). Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gammacarboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182: 626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DESCRIPTION OF THE INVENTION

The invention relates to novel pheS (beta) and pheS (alpha) polypeptides and polynucleotides as described in greater detail below. In particular, the invention relates to polypeptides and polynucleotides of a novel pheS (beta) and pheS (alpha) of Streptococcus pneumoniae, which is related by amino acid sequence homology to Bacillus subtilis phenylalanyl tRNA synthetase beta or alpha sub-unit polypeptide, respectively. The invention relates especially to pheS (beta) comprising the nucleotide and amino acid sequences set out in Table 1 [SEQ ID NO:1] and Table 1 [SEQ ID NO:2] respectively, and to the pheS (beta) nucleotide sequences of the DNA in the deposited strain and amino acid sequences encoded thereby. The invention also relates especially to pheS (alpha) comprising the nucleotide and amino acid sequences set out in Table 1 [SEQ ID NO:5] and Table 1 [SEQ ID NO:6] respectively, and to the pheS (alpha) nucleotide sequences of the DNA in the deposited strain and amino acid sequences encoded thereby.

TABLE 1 pheS (beta) and pheS (alpha) Polynucleotide and Polypeptide Sequences (A)
Sequences from *Streptococcus pneumoniae* pheS (beta) polynucleotide sequence
[SEQ ID NO: 1].

```
5'-1  ATGCTTGTAT  CTTATAAATG  GTTAAAAGAA  TTGGTGGACA  TTGATGTGCC
  51  ATCACAAGAG  TTGGCTGAAA  AAATGTCAAC  TACAGGGATC  GAGGTAGAGG
 101  GTGTCGAATT  ACCAGCTGCT  GGTCTCTCAA  AAATTGTCGT  CGGTGAGGTC
 151  TTGTCTTGCG  AAGCTGTGCC  AGAGACTCAC  CTCCATGTTT  GTCAGATTAA
 201  CGTTGGCGAA  GAAGAAGAGC  GTCAGATCGT  TTGTGGTGCC  CCAAATGTGC
 251  GTGCTGGGAT  CAAGGTCATG  GTGGCTCTTC  CAGGAGCTCG  TATCGCTGAT
 301  AACTACAAAA  TCAAAAAAGG  AAAAATCCGT  GGTTTGGAGT  CACTTGGAAT
 351  GATCTGTTCA  CTTGGTGAAT  TGGGAATTTC  TGACTCAGTT  GTGCCTAAGG
 401  AATTCGCAGA  TGGCATCCAA  ATCTTGCCTG  AAGATGCCGT  GCCAGGTGAG
 451  GAAGTCTTTT  CTTACCTAGA  CTTGGATGAT  GAAATCATCG  AACTTTCCAT
 501  CACACCAAAC  CGTGCAGATG  CCCTTTCTAT  GTGTGGAGTG  GCTCACGAAG
 551  TGGCAGCCAT  CTATGACAAG  GCAGTCAACT  TTAAAAAATT  TACTCTAACA
 601  GAAACTAATG  AAGCTGCGGC  AGATGCCCTT  TCTGTCAGCA  TTGAGACAGA
 651  CAAGGCGCCT  TACTATGCAG  CTCGTATCTT  GGACAATGTG  ACTATCGCAC
 701  CAAGTCCACA  ATGGTTGCAA  AACCTTCTCA  TGAACGAAGG  CATCCGTCCC
 751  ATCAATAACG  TTGTAGACGT  GACAAACTAC  ATCCTGCTCT  ACTTTGGTCA
 801  ACCTATGCAT  GCTTTTGACT  TGGACACATT  TGAAGGGACT  GACATCCGTG
 851  TGCGTGAAGC  GCGTGATGGT  GAAAAATTAG  TGACCCTGGA  CGGTGAAGAA
 901  CGAGACTTGG  CTGAGACAGA  CCTCGTGATT  ACAGTTGCTG  ACAAACCAGT
 951  AGCCCTTGCC  GGTGTTATGG  GTGGTCAGGC  TACAGAAATT  TCTGAAAAAT
1001  CTAGTCGTGT  TATCCTTGAA  GCTGCTGTTT  TTAATGGCAA  ATCTATCCGT
1051  AAGACAAGTG  GTCGCCTGAA  CCTTCGTTCT  GAGTCATCTT  CTCGCTTTGA
1101  AAAAGGAATT  AATGTGGCAA  CAGTTAATGA  AGCCCTTGAT  GCGGCAGCTA
1151  GCATGATTGC  AGAGCTTGCA  GGCGCGACGG  TGCGTAAGGG  TATCGTTTCA
1201  GCGGGTGAGC  TTGATACCTC  TGATGTGGAA  GTTTCTTCAA  CCCTTGCTGA
1251  TGTTAACCGT  GTCCTCGGAA  CTGAGCTGTC  TTATGCTGAT  GTANAAGACG
1301  TCTTCCGTCG  TCTTGGCTTT  GGTCTTTCTG  GAAATGCAGA  CAGCTTTACA
1351  GTCAGCGTAC  CACGTCGTCG  TTGGGATATC  ACAATCGAAG  CTGATCTCTT
1401  TGAAGAAATC  GCTCGTATCT  ATGGATATGA  CCGCTTGCCA  ACCAGCCTTC
1451  CAAAAGACGA  TGGTACAGCT  GGTGAATTGA  CTGTGATACA  AAAACTCCGC
1501  CGTCAAGTTC  GTACCATTGC  TGAAGGAGCA  GGTTTGACAG  AAATCATCAC
1551  CTATGCTCTG  ACAACTCCTG  AAAAAGCAGT  TGAGTTCACA  GCTCAACCAA
1601  GTAACCTTAC  TGAACTCATG  TGGCCAATGA  CTGTGGATCG  TTCAGTCCTC
1651  CGTCAAAATA  TGATTTCAGG  GATCCTTGTT  ACCGTTGCCT  ACAACGTGGC
1701  TCGTAAGAAT  AAAAACTTGG  CCCTTTATGA  GATTGAAAAA  GTCTTTGAAC
1751  AAACAGGTAA  TCCAAAAGAA  GAACTTCCAA  ATGAGATCAA  CAGCTTTGCC
1801  TTTGCTTTGA  CAGGCTTGGT  TGCTGAAANA  GATTTCCAAA  CAGCAGCAGT
1851  TCCAGTTGAT  TTTTTTTATG  CTAAGGGAAT  CCTTGAAGCC  NTAITTACTC
1901  GTTTGGGACT  CCAAGTAACC  TATACAGCAA  CATCTGAAAT  CGNTAGCCTT
1951  CATCCAGGTC  GTACAGCCGT  GATTTCACTC  GGTGACCAAG  TTCTTGGTTT
2001  CCTTGGCCAA  GTGCATCCAG  TCACTGCCAA  GGCTTACGAT  ATTCCAGAAA
2051  CGTATGTAGC  TGAGCTTAAC  CTTTCAGCCA  TCGAAGGGGC  GCTCCAACCT
2101  GCTGTTCCAT  TTGTGAAAAT  CACCAGATTC  CCAGCAGTCA  GCCGTGACGT
2151  TGCCTTTCTC  CTCAAGGCAG  AAGTGACTCA  CCAAGCAGTT  GTAGATGCTA
2201  TCCAAGCTGC  CGGCGTGAAA  CGTTTGACAG  ATATCAGACT  CTTTGACGTC
2251  TTCTCAGGTG  AAAAACTGGG  ACTTGGTATG  AAGTCAATGG  CTTATAGCTT
2301  GACCTTCCAA  AATCCAGAAG  ACAGCTTAAC  GGACGAAGAA  GTCGCACGCT -3'
```

(B)
pheS (beta) polypeptide sequence deduced from the polynucleotide sequence in this table
[SEQ ID NO: 2].

```
NH2-1  MLVSYKWLKE  LVDIDVPSQE  LAEKMSTTGI  EVEGVELPAA  GLSKIVVGEV
   51  LSCEAVPETH  LHVCQINVGE  EEERQIVCGA  PNVRAGIKVM  VALPGARIAD
  101  NYKIKKGKIR  GLESLGMICS  LGELGISDSV  VPKEFADGIQ  ILPEDAVPGE
  151  EVFSYLDLDD  EIIELSITPN  RADALSMCGV  AHEVAAIYDK  AVNFKKFTLT
  201  ETNEAAADAL  SVSIETDKAP  YYAARILDNV  TIAPSPQWLQ  NLLMNEGIRP
  251  INNVVDVTNY  ILLYFGQPMH  AFDLDTFEGT  DIRVREARDG  EKLVTLDGEE
  301  RDLAETDLVI  TVADKPVALA  GVMGGQATEI  SEKSSRVILE  AAVFNGKSIR
  351  KTSGRLNLRS  ESSSRFEKGI  NVATVNEALD  AAASMIAELA  GATVRKGIVS
  401  AGELDTSDVE  VSSTLADVNR  VLGTELSYAD  VXDVFRRLGF  GLSGNADSFT
  451  VSVPRRRWDI  TIEADLFEEI  ARIYGYDRLP  TSLPKDDGTA  GELTVIQKLR
  501  RQVRTIAEGA  GLTEIITYAL  TIPEKAVEFT  AQPSNLTELM  WPMTVDRSVL
  551  RQNMISGILV  TVAYNVARKN  KNLALYEIGK  VFEQTGNPKE  ELPNEINSFA
  601  FALTGLVAEX  DFQTAAVPVD  FFYAKGILEA  XFTRLGLQVT  YTATSEIXSL
  651  HPGRTAVISL  GDQVLGFLGQ  VHPVTAKAYD  IPETYVAELN  LSAIEGALQP
  701  AVPFVEITRF  PAVSRDVAFL  LKAEVTHQAV  VDAIQAAGVK  RLTDIRLFDV
```

TABLE 1-continued pheS (beta) and pheS (alpha) Polynucleotide and Polypeptide Sequences

|  |  |  |  |  |
|---|---|---|---|---|
| 751 FSGEKLGLGM | KSMAYSLTFQ | NPEDSLTDEE | VAR-COOH | |

(C)

pheS (beta) polynucleotide sequence embodiments
[SEQ ID NO: 1].

| | | | | |
|---|---|---|---|---|
| X—(R$_1$)$_n$-1 ATGCTTGTAT | CTTATAAATG | GTTAAAAGAA | TTGGTGGACA | TTGATGTGCC |
| 51 ATCACAAGAG | TTGGCTGAAA | AAATGTCAAC | TACAGGGATC | GAGGTAGAGG |
| 101 GTGTCGAATT | ACCAGCTGCT | GGTCTCTCAA | AAATTGTCGT | CGGTGAGGTC |
| 151 TTGTCTTGCG | AAGCTGTGCC | AGAGACTCAC | CTCCATGTTT | GTCAGATTAA |
| 201 CGTTGGCGAA | GAAGAAGAGC | GTCAGATCGT | TTGTGGTGCC | CCAAATGTGC |
| 251 GTGCTGGGAT | CAAGGTCATG | GTGGCTCTTC | CAGGAGCTCG | TATCGCTGAT |
| 301 AACTACAAAA | TCAAAAAAGG | AAAAATCCGT | GGTTTGGAGT | CACTTGGAAT |
| 351 GATCTGTTCA | CTTGGTGAAT | TGGGAATTTC | TGACTCAGTT | GTGCCTAAGG |
| 401 AATTCGCAGA | TGGCATCCAA | ATCTTGCCTG | AAGATGCCGT | GCCAGGTGAG |
| 451 GAAGTCTTTT | CTTACCTAGA | CTTGGATGAT | GAAATCATCG | AACTTTCCAT |
| 501 CACACCAAAC | CGTGCAGATG | CCCTTTCTAT | GTGTGGAGTG | GCTCACGAAG |
| 551 TGGCAGCCAT | CTATGACAAG | GCAGTCAACT | TTAAAAAATT | TACTCTAACA |
| 601 GAAACTAATG | AAGCTGCGGC | AGATGCCCTT | TCTGTCAGCA | TTGAGACAGA |
| 651 CAAGGCGCCT | TACTATGCAG | CTCGTATCTT | GGACAATGTG | ACTATCGCAC |
| 701 CAAGTCCACA | ATGGTTGCAA | AACCTTCTCA | TGAACGAAGG | CATCCGTCCC |
| 751 ATCAATAACG | TTGTAGACGT | GACAAACTAC | ATCCTGCTCT | ACTTTGGTCA |
| 801 ACCTATGCAT | GCTTTTGACT | TGGACACATT | TGAAGGGACT | GACATCCGTG |
| 851 TGCGTGAAGC | GCGTGATGGT | GAAAAATTAG | TGACCCTGGA | CGGTGAAGAA |
| 901 CGAGACTTGG | CTGAGACAGA | CCTCGTGATT | ACAGTTGCTG | ACAAACCAGT |
| 951 AGCCCTTGCC | GGTGTTATGG | GTGGTCAGGC | TACAGAAATT | TCTGAAAAAT |
| 1001 CTAGTCGTGT | TATCCTTGAA | GCTGCTGTTT | TTAATGGCAA | ATCTATCCGT |
| 1051 AAGACAAGTG | GTCCGCCTGAA | CCTTCGTTCT | GAGTCATCTT | CTCGCTTTGA |
| 1101 AAAAGGAATT | AATGTGGCAA | CAGTTAATGA | AGCCCTTGAT | GCGGCAGCTA |
| 1151 GCATGATTGC | AGAGCTTGCA | GGCGCGACGG | TGCGTAAGGG | TATCGTTTCA |
| 1201 GCGGGTGAGC | TTGATACCTC | TGATGTGGAA | GTTTCTTCAA | CCCTTGCTGA |
| 1251 TGTTAACCGT | GTCCTCGGAA | CTGAGCTGTC | TTATGCTGAT | GTANAAGACG |
| 1301 TCTTCCGTCG | TCTTGGCTTT | GGTCTTTCTG | GAAATGCAGA | CAGCTTTACA |
| 1351 GTCAGCGTAC | CACGTCGTCG | TTGGGATATC | ACAATCGAAG | CTGATCTCTT |
| 1401 TGAAGAAATC | GCTCGTATCT | ATGGATATGA | CCGCTTGCCA | ACCAGCCTTC |
| 1451 CAAAAGACGA | TGGTACAGCT | GGTGAATTGA | CTGTGATACA | AAAACTCCGC |
| 1501 CGTCAAGTTC | GTACCATTGC | TGAAGGAGCA | GGTTTGACAG | AAATCATCAC |
| 1551 CTATGCTCTG | ACAACTCCTG | AAAAAGCAGT | TGAGTTCACA | GCTCAACCAA |
| 1601 GTAACCTTAC | TGAACTCATG | TGGCCAATGA | CTGTGGATCG | TTCAGTCCTC |
| 1651 CGTCAAAATA | TGATTTCAGG | GATCCTTGTT | ACCGTTGCCT | ACAACGTGGC |
| 1701 TCGTAAGAAT | AAAAACTTGG | CCCTTTATGA | GATTGGAAAA | GTCTTTGAAC |
| 1751 AAACAGGTAA | TCCAAAAGAA | GAACTTCCAA | ATGAGATCAA | CAGCTTTGCC |
| 1801 TTTGCTTTGA | CAGGCTTGGT | TGCTGAAANA | GATTTCCAAA | CAGCAGCAGT |
| 1851 TCCAGTTGAT | TTTTTTTATG | CTAAGGGAAT | CCTTGAAGCC | NTATTTACTC |
| 1901 GTTTGGGACT | CCAAGTAACC | TATACAGCAA | CATCTGAAAT | CGNTAGCCTT |
| 1951 CATCCAGGTC | GTACAGCCGT | GATTTCACTC | GGTGACCAAG | TTCTTGGTTT |
| 2001 CCTTGGCCAA | GTGCATCCAG | TCACTGCCAA | GGCTTACGAT | ATTCCAGAAA |
| 2051 CGTATGTAGC | TGAGCTTAAC | CTTTCAGCCA | TCGAAGGGGC | GCTCCAACCT |
| 2101 GCTGTTCCAT | TTGTGGAAAT | CACCCAGATTC | CCAGCAGTCA | GCCGTGACGT |
| 2151 TGCCTTTCTC | CTCAAGGCAG | AAGTGACTCA | CCAAGCAGTT | GTAGATGCTA |
| 2201 TCCAAGCTGC | CGGCGTGAAA | CGTTTGACAG | ATATCAGACT | CTTTGACGTC |
| 2251 TTCTCAGGTG | AAAAACTGGG | ACTTGGTATG | AAGTCAATGG | CTTATAGCTT |
| 2301 GACCTTCCAA | AATCCAGAAG | ACAGCTTAAC | GGACGAAGAA | GTCGCACGCT |

(D)

pheS (beta) polypeptide sequence embodiments
[SEQ ID NO: 2].

| | | | | |
|---|---|---|---|---|
| X—(R$_1$)$_n$-1 MLVSYKWLKE | LVDIDVPSQE | LAEKMSTTGI | EVEGVELPAA | GLSKIVVGEV |
| 51 LSCEAVPETH | LHVCQINVGE | EEERQIVCGA | PNVRAGIKVM | VALPGARIAD |
| 101 NYKIKKGKIR | GLESLGMICS | LGELGISDSV | VPKEFADGIQ | ILPEDAVPGE |
| 151 EVFSYLDLDD | EIIELSITPN | RADALSMCGV | AHEVAAIYDK | AVNFKKFTLT |
| 201 ETNEAAADAL | SVSIETDKAP | YYAARILDNV | TIAPSPQWLQ | NLLMNEGIRP |
| 251 INNVVDVTNY | ILLYFGQPMH | AFDLDTFEGT | DIRVREARDG | EKLVTLDGEE |
| 301 RDLAETDLVI | TVADKPVALA | GVMGGQATEI | SEKSSRVILE | AAVFNGKSIR |
| 351 KTSGRLNLRS | ESSSRFEKGI | NVATVNEALD | AAASMIAELA | GATVRKGIVS |
| 401 AGELDTSDVE | VSSTLADVNR | VLGTELSYAD | VXDVFRRLGF | GLSGNADSFT |
| 451 VSVPRRRWDI | TIEADLFEEI | ARIYGYDRLP | TSLPKDDGTA | GELTVIQKLR |
| 501 RQVRTIAEGA | GLTEIITYAL | TIPEKAVEFT | AQPSNLTELM | WPMTVDRSVL |
| 551 RQNMISGILV | TVAYNVARKN | KNLALYEIGK | VFEQTGNPKE | ELPNEINSFA |
| 601 FALTGLVAEX | DFQTAAVPVD | FFYAKGILEA | XFTRLGLQVT | YTATSEIXSL |
| 651 HPGRTAVISL | GDQVLGFLGQ | VHPVTAKAYD | TPETYVAELN | LSAIEGALQP |
| 701 AVPFVEITRF | PAVSRDVAFL | LKAEVTHQAV | VDAIQAAGVK | RLTDIRLFDV |
| 751 FSGEKLGLGM | KSMAYSLTFQ | NPEDSLTDEE | VAR-(R$_2$)$_n$-Y | |

(E)

Sequences from *Streptococcus pneumoniae* pheS (beta) polynucleotide ORF sequence
[SEQ ID NO: 3].

| | | | | |
|---|---|---|---|---|
| 5'-1 CGTATCGCTG | ATAACTACAA | AATCAAAAAA | GGAAAAATCC | GTGGTTTGGA |

TABLE 1-continued pheS (beta) and pheS (alpha) Polynucleotide and Polypeptide Sequences

```
 51 GTCACTTGGA ATGATCTGTT CACTTGGTGA ATTGGGAATT TCTGACTCAG
101 TTGTGCCTAA GGAATTCGCA GATGGCATCC AAATCTTGCC TGAAGATGCC
151 GTGCCAGGTG AGGAAGTCTT TTCTTACCTA GACTTGGATG ATGAAATCAT
201 CGAACTTTCC ATCACACCAA ACCGTGCAGA TGCCCTTTCT ATGTGTGGAG
251 TGGCTCACGA AGTGGCAGCC ATCTATGACA AGGCAGTCAA CTTTAAAAAA
301 TTTACTCTAA CAGAAACTAA TGAAGCTGCG GCAGATGCCC TTTCTGTCAG
351 CATTGAGACA GACAAGGCGC CTTACTATGC AGCTCGTATC TTGGACAATG
401 TGACTATCGC ACCAAGTCCA CAATGGTTGC AAAACCTTCT CATGAACGAA
451 GCATC-3'
```
(F)

pheS (beta) polypeptide sequence deduced from the polynucleotide ORF sequence in this table
[SEQ ID NO: 4].

```
NH₂-1 RIADNYKIKK GKIRGLESLG MICSLGELGI SDSVVPKEFA DGIQILPEDA
   51 VPGEEVFSYL DLDDEIIELS ITPNRADALS MCGVAHEVAA IYDKAVNFKK
  101 FTLTETNEAA ADALSVSIET DKAPYYAARI LDNVTIAPSP QWLQNLLMNE
  151 A-COOH
```
(G)

pheS (alpha) sequences from *Streptococcus pneumoniae* pheS (alpha) polynucleotide sequence
[SEQ ID NO: 5].

```
 5'-1 GGATCCCCCG GGCTGCAGGA ATTAAAAGCG CTTCGCGAAG AAACGCTGAC
   51 TAGCTTGAAG CAGATTACTG CTGGAAATGA AAAAGAGATG CAAGATTTGC
  101 GTGTCTCTGT CCTTGGTAAA AAGGGTTCGC TTACTGAAAT CCTCAAAGGG
  151 ATGAAAGATG TTTCTGCTGA GATGCGTCCA ATCATCGGGA AACACGTCAA
  201 TGAAGCTCGT GATGTCTTGA CAGCTGCTTT TGAAGAAACA GCTAAGCTCT
  251 TGGAAGAAAA GAAAGTCGCG GCTCAACTGG CTAGCGAGAG TATCGATGTG
  301 ACGCTTCCAG GTCGTCCAGT TGCGACTGGT CACCGTCACG TTTTGACACA
  351 AACCAGTGAA GAAATCGAAG ATATCTTCAT CGGTATGGGT TATCAAGTCG
  401 TGGATGGTTT TGAAGTGGAG CAAGACTACT ATAACTTTGA ACGTATGAAC
  451 CTTCCAAAAG ACCACCCAGC TCGTGATATG CAGGATACTT TCTATATCAC
  501 TGAAGAAATC TTGCTCCGTA CCCACACGTC TCCAGTTCAG GCACGTGCTA
  551 TGGATGCCCA TGATTTTTCT AAAGGTCCTT TGAAGATAAT CTCGCCAGGG
  601 CGTGTCTTCC GTCGCGATAC GGACGATGCG ACCCACAGTC ACCAATTCCA
  651 CCAAATCGAA GGCTTGGTAG TTGGGAAAAA TATCTCTATG GCTGATCTTC
  701 AAGGAACGCT TCAGTTGATT GTCCAAAAAA TGTTTGGTGA AGAGCGTCAA
  751 ATTCGTTTGC GTCCATCTTA CTTCCCATTC ACAGAGCCAT CTGTTGAGGT
  801 GGATGTTTCT TGCTTCAAAT GTGGTGGAGA AGGCTGTAAC GTATGTAAGA
  851 AAACAGGTTG GATCGAAATT ATGGGGGCCG GTATGGTTCA CCCACGTGTC
  901 CTTGAAATGA GTGGTATCGA TGCGACTGTA TACTCTGGCT TTGCCTTTGG
  951 TCTTGGACAA GAGCGTGTAG CTATGCTCCG TTATGGAATC AACGATATCC
 1001 GTGGATTCTA CCAAGGAGAT GTCCGCTTCT CAGAACAGTT TAAATAA-3'
```
(H)

pheS (alpha) polypeptide sequence deduced from the polynucleotide sequence in this table
[SEQ ID NO: 6].

```
NH₂-1 GSPGLQELKA LREETLTSLK QITAGNEKEM QDLRVSVLGK KGSLTEILKG
   51 MKDVSAEMRP IIGKHVNEAR DVLTAAFEET AKLLEEKKVA AQLASESIDV
  101 TLPGRPVATG HRHVLTQTSE EIEDIFIGMG YQVVDGFEVE QDYYNFERMN
  151 LPKDHPARDM QDTFYITEEI LLRTHTSPVQ ARAMDAHDFS KGPLKIISPG
  201 RVFRRDTDDA THSHQFHQIE GLVVGKNISM ADLQGTLQLI VQKMFGEERQ
  251 IRLRPSYFPF TEPSVEVDVS CFKCGGEGCN VCKKTGWIEI MGAGMVHPRV
  301 LEMSGIDATV YSGFAFGLGQ ERVAMLRYGI NDIRGFYQGD VRFSEQFK-COOH
```
(I)

pheS (alpha) polynucleotide sequence embodiments
[SEQ ID NO: 5].

```
X—(R₁)ₙ-1 GGATCCCCCG GGCTGCAGGA ATTAAAAGCG CTTCGCGAAG AAACGCTGAC
      51 TAGCTTGAAG CAGATTACTG CTGGAAATGA AAAAGAGATG CAAGATTTGC
     101 GTGTCTCTGT CCTTGGTAAA AAGGGTTCGC TTACTGAAAT CCTCAAAGGG
     151 ATGAAAGATG TTTCTGCTGA GATGCGTCCA ATCATCGGGA AACACGTCAA
     201 TGAAGCTCGT GATGTCTTGA CAGCTGCTTT TGAAGAAACA GCTAAGCTCT
     251 TGGAAGAAAA GAAAGTCGCG GCTCAACTGG CTAGCGAGAG TATCGATGTG
     301 ACGCTTCCAG GTCGTCCAGT TGCGACTGGT CACCGTCACG TTTTGACACA
     351 AACCAGTGAA GAAATCGAAG ATATCTTCAT CGGTATGGGT TATCAAGTCG
     401 TGGATGGTTT TGAAGTGGAG CAAGACTACT ATAACTTTGA ACGTATGAAC
     451 CTTCCAAAAG ACCACCCAGC TCGTGATATG CAGGATACTT TCTATATCAC
     501 TGAAGAAATC TTGCTCCGTA CCCACACGTC TCCAGTTCAG GCACGTGCTA
     551 TGGATGCCCA TGATTTTTCT AAAGGTCCTT TGAAGATAAT CTCGCCAGGG
     601 CGTGTCTTCC GTCGCGATAC GGACGATGCG ACCCACAGTC ACCAATTCCA
     651 CCAAATCGAA GGCTTGGTAG TTGGGAAAAA TATCTCTATG GCTGATCTTC
     701 AAGGAACGCT TCAGTTGATT GTCCAAAAAA TGTTTGGTGA AGAGCGTCAA
     751 ATTCGTTTGC GTCCATCTTA CTTCCCATTC ACAGAGCCAT CTGTTGAGGT
     801 GGATGTTTCT TGCTTCAAAT GTGGTGGAGA AGGCTGTAAC GTATGTAAGA
     851 AAACAGGTTG GATCGAAATT ATGGGGGCCG GTATGGTTCA CCCACGTGTC
     901 CTTGAAATGA GTGGTATCGA TGCGACTGTA TACTCTGGCT TTGCCTTTGG
     951 TCTTGGACAA GAGCGTGTAG CTATGCTCCG TTATGGAATC AACGATATCC
```

TABLE 1-continued pheS (beta) and pheS (alpha) Polynucleotide and Polypeptide Sequences

```
1001 GTGGATTCTA  CCAAGGAGAT  GTCCGCTTCT  CAGAACAGTT  TAAATAA
—(R₂)ₙ—Y
```
(J)

pheS (alpha) polypeptide sequence embodiments
[SEQ ID NO: 6].

```
X—(R₁)ₙ-1 GSPGLQELKA  LREETLTSLK  QITAGNEKEM  QDLRVSVLGK  KGSLTEILKG
       51 MKDVSAEMRP  IIGKHVNEAR  DVLTAAFEET  AKLLEEKKVA  AQLASESIDV
      101 TLPGRPVATG  HRHVLTQTSE  EIEDIFIGMG  YQVDDGFEVE  QDYYNFERMN
      151 LPKDHPARDM  QDTFYITEEI  LLRTHTSPVQ  ARAMDAHDFS  KGPLKIISPG
      201 RVFRRDTDDA  THSHQFHQIE  GLVVGKNISM  ADLQGTLQLI  VQKMFGEERQ
      251 IRLRPSYFPF  TEPSVEVDVS  CFKCGGEGCN  VCKKTGWIEI  MGAGMVHPRV
      301 LEMSGIDATV  YSGFAFGLGQ  ERVAMLRYGI  NDIRGFYQGD  VRFSEQFK
—(R₂)ₙ—Y
```
(K)

Sequences from *Streptococcus pneumoniae* pheS (alpha) polynucleotide ORF sequence
[SEQ ID NO: 7].

```
5'-1 CAATTCCACC  AAATCGAAGG  CTTGGTAGTT  GGGAAAAATA  TCTCTATGGC
  51 TGATCTTCAA  GGAACGCTTC  AGTTGATTGT  CCAAAAAATG  TCTGGTGAAG
 101 AGCGTCAAAT  TCGTTTGCGT  CCATCTTACT  TCCCATTCAC  ACACCCATCT
 151 GTTGAGGTGG  ATGTTTCTTG  CTTCAAATGT  GGTGGAGAAG  GCTGTAA-3'
```
(L)

pheS (alpha) polypeptide sequence deduced from the polynucleotide ORF sequence in this table
[SEQ ID NO: 8].

```
NH₂-1 QFHQIEGLVV  GKNISMADLQ  GTLQLIVQKM  SGEERQIRLR  PSYFPFTHPS
   51 VEVDVSCFKC  GGEGC-COOH
```

Deposited Materials

A deposit containing a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on 11 Apr. 1996 and assigned deposit number 40794. The deposit was described as *Streptococcus pneumoniae* 0100993 on deposit. On 17 Apr. 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain contains both the full length pheS (beta) and pheS (alpha) genes. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

Polypeptides

The polypeptides of the invention include the polypeptides of Table 1 [SEQ ID NO:2, 4, 6, 8] (in particular the mature polypeptide) as well as polypeptides and fragments, particularly those which have the biological activity of pheS (beta) and/or pheS (alpha), and also those which have at least 70% identity to a polypeptide of Table 1 [SEQ ID NOS: 2, 4, 6, 8] or the relevant portion, preferably at least 80% identity to a polypeptide of Table 1 [SEQ ID NOS: 2, 4 6, 8], and more preferably at least 90% similarity (more preferably at least 90% identity) to a polypeptide of Table 1 [SEQ ID NOS: 2, 4, 6, 8] and still more preferably at least 95% similarity (still more preferably at least 95% identity) to a polypeptide of Table 1 [SEQ ID NOS: 2, 4, 6, 8] and also include portions of such polypeptides with such portion of the polypeptide generally containing at least 30 amino acids and more preferably at least 50 amino acids.

The invention also includes polypeptides of the formula set forth in Table 1 (D and J) [SEQ ID NO:2, 6] wherein, at the amino terminus, X is hydrogen, and at the carboxyl terminus, Y is hydrogen or a metal, $R_1$ and $R_2$ is any amino acid residue, and n is an integer between 1 and 1000. Any stretch of amino acid residues denoted by either R group, where R is greater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with pheS (beta) and pheS (alpha) polypeptides fragments may be "free-standing," or comprised within a larger polypeptide of which they form a part or region, most preferably as a single continuous region, a single larger polypeptide.

Preferred fragments include, for example, truncation polypeptides having a portion of an amino acid sequence of Table 1 [SEQ ID NOS: 2, 4, 6, 8], or of variants thereof, such as a continuous series of residues that includes the amino terminus, or a continuous series of residues that includes the carboxyl terminus. Degradation forms of the polypeptides of the invention in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of pheS (beta) and/or pheS (alpha), including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of Streptococcus pneumoniae or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

In addition to the standard one letter amino acid codes, the term "X" is also used in certain of the polynucleotide embodiments herein (see Table 1). "X" means that any of the twenty naturally occurring amino acids may appear at such a designated position in the polypetide sequence.

Polynucleotides

Another aspect of the invention relates to isolated polynucleotides that encode the pheS (beta) or pheS (alpha) polypeptide having a deduced amino acid sequence of Table 1 [SEQ ID NOS: 2, 4, 6, 8] and polynucleotides closely related thereto and variants thereof.

Using the information provided herein, such as a polynucleotide sequence set out in Table 1 [SEQ ID NOS: 1, 3, 5, 7], a polynucleotide of the invention encoding pheS (beta) and/or pheS (alpha) polypeptide may be obtained using standard cloning and screening methods, such as those for cloning and sequencing chromosomal DNA fragments from bacteria using Streptococcus pneumoniae 0100993 cells as starting material, followed by obtaining a full length clone. For example, to obtain a polynucleotide sequence of the invention, such as a sequence given in Table 1 [SEQ ID NOS: 1, 3, 5, 7], typically a library of clones of chromosomal DNA of Streptococcus pneumoniae 0100993 in E. coli or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E.F. and Sambrook et al., MOLECULAR CLONING, A LABORATORY MANUAL, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Illustrative of the invention, the polynucleotide set out in Table 1 [SEQ ID NO:1] was discovered in a DNA library derived from Streptococcus pneumoniae 0100993.

The DNA sequence set out in Table 1 [SEQ ID NOS: 1, 5] contains an open reading frame encoding a protein having about the number of amino acid residues set forth in Table 1 [SEQ ID NOS: 2, 6 respectively] with a deduced molecular weight that can be calculated using amino acid residue molecular weight values well known in the art. The start codon of the DNA of full length pheS (beta) in Table 1 is nucleotide number 1 and last codon that encodes an amino acid is number 2350, the stop codon being the next codon following this last codon encoding an amino acid. The start codon of the DNA of full length pheS (alpha) in Table 1 is nucleotide number 1 and last codon that encodes an amino acid is number 1044, the stop codon being the next codon following this last codon encoding an amino acid.

pheS (beta) and pheS (alpha) of the invention is structurally related to other proteins of the phenylalanyl tRNA synthetase (alpha and beta sub-unit) family, as shown by the results of sequencing the DNA encoding pheS (beta) and pheS (alpha) of the deposited strain. The pheS (beta) protein exhibits greatest homology to Bacillus subtilis phenylalanyl tRNA synthetase beta sub-unit protein among known proteins. pheS (beta) of Table 1 [SEQ ID NO:2] has about 47% identity over its entire length and about 64% similarity over its entire length with the amino acid sequence of Bacillus subtilis phenylalanyl tRNA synthetase beta sub-unit polypeptide. The pheS (alpha) protein exhibits greatest homology to Bacillus subtilis phenylalanyl tRNA synthetase (alpha sub-unit) protein among known proteins. pheS (alpha) of Table 1 [SEQ ID NO:6] has about 62% identity over its entire length and about 75% similarity over its entire length with the amino acid sequence of Bacillus subtilis phenylalanyl tRNA synthetase (alpha sub-unit) polypeptide.

The invention provides a polynucleotide sequence identical over its entire length to each full length coding sequence in Table 1 [SEQ ID NO:1, 5]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro- protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci., USA 86: 821–824 (1989), or an HA tag (Wilson et al., Cell 37: 767 (1984). Polynucleotides of the invention also include, but are not limited to, polynucleotides comprising a structural gene and its naturally associated sequences that control gene expression.

A preferred embodiment of the invention is the polynucleotide of comprising nucleotide 1 to 2034 set forth in SEQ ID NO:1 of Table 1 which encodes the pheS (beta) polypeptide. A further preferred embodiment of the invention is the polynucleotide of comprising nucleotide 1 to 915 set forth in SEQ ID NO:5 of Table 1 which encodes the pheS (alpha) polypeptide.

The invention also includes polynucleotides of the formula set forth in Table 1 (C and D)[SEQ ID NO:1 and 5 respectively] wherein, at the 5' end of the molecule, X is hydrogen, and at the 3' end of the molecule, Y is hydrogen or a metal, $R_1$ and $R_2$ is any nucleic acid residue, and n is an integer between 1 and 1000. Any stretch of nucleic acid residues denoted by either R group, where R is greater than 1, may be either a heteropolymer or a homopolymer, preferably a heteropolymer.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* pheS (beta) or pheS (alpha) comprising the amino acid sequence set out in Table 1 [SEQ ID NO:2 and 6 respectively]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

In addition to the standard A, G, C, T/U representations for nucleic acid bases, the term "N" is also used in polynucleotide sequences herein. "N" means that any of the four DNA or RNA bases may appear at such a designated position in the DNA or RNA sequence, except that N cannot be a base that when taken in combination with adjacent nucleotide positions, when read in the correct reading frame, would have the effect of generating a premature termination codon in such reading frame.

The invention further relates to variants of the polynucleotides described herein that encode for variants of the polypeptide having a deduced amino acid sequence of Table 1 [SEQ ID NO:2, 6]. Variants that are fragments of the polynucleotides of the invention may be used to synthesize full-length polynucleotides of the invention.

Further particularly preferred embodiments are polynucleotides encoding pheS (beta) and/or pheS (alpha) variants, that have the amino acid sequence of pheS (beta) or pheS (alpha) polypeptide of Table 1 [SEQ ID NO:2 and 6 respectively] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of pheS (beta) or pheS (alpha)

Further preferred embodiments of the invention are polynucleotides that are at least 70% identical over their entire length to a polynucleotide encoding pheS (beta) and/or pheS (alpha) polypeptide having an amino acid sequence set out in Table 1 [SEQ ID NOS: 2, 4, 6, 8], and polynucleotides that are complementary to such polynucleotides. Alternatively, most highly preferred are polynucleotides that comprise a region that is at least 80% identical over its entire length to a polynucleotide encoding pheS (beta) and/or pheS (alpha) polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides that encode polypeptides that retain substantially the same biological function or activity as the mature polypeptide encoded by the DNA of Table 1 [SEQ ID NO:1, 5].

The invention further relates to polynucleotides that hybridize to the herein abovedescribed sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5× SSC (150mM NaCl, 15mM trisodium citrate), 50 mM sodium phosphate (pH7.6), 5× Denhardt's solution, 10% dextran sulfate, and 20 micrograms/ml denatured, sheared salmon sperm DNA, followed by washing the hybridization support in 0.1× SSC at about 65° C. Hybridization and wash conditions are well known and exemplified in Sambrook, et at., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 or SEQ ID NO:5 under stringent hybridization conditions with a probe having the sequence of said polynucleotide sequence set forth in SEQ ID NO:1 or SEQ ID NO:5 respectively or a fragment thereof; and isolating said DNA sequence. Fragments useful for obtaining such a polynucleotide include, for example, probes and primers described elsewhere herein.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding pheS (beta) and/or pheS (alpha) and to isolate cDNA and genomic clones of other genes that have a high sequence similarity to the pheS (beta) and/or pheS (alpha) gene. Such probes generally will comprise at least 15 bases. Preferably, such probes will have at least 30 bases and may have at least 50 bases. Particularly preferred probes will have at least 30 bases and will have 50 bases or less.

For example, the coding region of the pheS (beta) and/or pheS (alpha) gene may be isolated by screening using the DNA sequence provided in SEQ ID NO:1 or 5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

The polynucleotides and polypeptides of the invention may be employed, for example, as research reagents and materials for discovery of treatments of and diagnostics for disease, particularly human disease, as further discussed herein relating to polynucleotide assays.

Polynucleotides of the invention that are oligonucleotides derived from the sequences of SEQ ID NOS: 1 and/or 2 and/or 5 and/or 6 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., *BASIC METHODS IN MOLECULAR BIOLOGY*, (1986) and Sambrook et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci *E. coli*, streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic Assays

This invention is also related to the use of the pheS (beta) and/or pheS (alpha) polynucleotides of the invention for use as diagnostic reagents. Detection of pheS (beta) and/or pheS (alpha) in a eukaryote, particularly a mammal, and especially a human, will provide a diagnostic method for diagnosis of a disease. Eukaryotes (herein also "individual(s)"), particularly mammals, and especially humans, infected with an organism comprising the pheS (beta) and/or pheS (alpha) gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled pheS (beta) and/or pheS (alpha) polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science*, 230: 1242 (1985). Sequence changes at specific locations also may be revealed by nuclease protection assays, such as RNase and S 1 protection or a chemical cleavage method. See, e.g., Cotton et al., *Proc. Natl. Acad. Sci., USA*, 85: 4397–4401 (1985).

Cells carrying mutations or polymorphisms in the gene of the invention may also be detected at the DNA level by a variety of techniques, to allow for serotyping, for example.

For example, RT-PCR can be used to detect mutations. It is particularly preferred to used RT-PCR in conjunction with automated detection systems, such as, for example, GeneScan. RNA or cDNA may also be used for the same purpose. PCR or RT-PCR. As an example, PCR primers complementary to a nucleic acid encoding pheS (beta) and/or pheS (alpha) can be used to identify and analyze mutations. The invention further provides these primers with 1, 2, 3 or 4 nucleotides removed from the 5' and/or the 3' end. These primers may be used for, among other things, amplifying pheS (beta) and/or pheS (alpha) DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Streptococcus pneumoniae*, and most preferably *otitis media, conjunctivitis, pneumonia, bacteremia, meningitis, sinusitis, pleural empyema and endocarditis, and most particularly meningitis, such as for example infection of cerebrospinal fluid, comprising determining from a sample derived from an individual a increased level of expression of polynucleotide comprising a sequence of Table 1 [SEQ ID NO:1 and/or 5]*. Increased or decreased expression of pheS (beta) and/or pheS (alpha) polynucleotide can be measured using any on of the methods well known in the art for the quantitation of polynucleotides, such as, for example, amplification, PCR, RT-PCR, RNase protection, Northern blotting and other hybridization methods.

In addition, a diagnostic assay in accordance with the invention for detecting overexpression of pheS (beta) and/or pheS (alpha) protein compared to normal control tissue samples may be used to detect the presence of an infection, for example. Assay techniques that can be used to determine levels of a pheS (beta) and/or pheS (alpha) protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

Antibodies generated against the polypeptides of the invention can be obtained by administering the polypeptides or epitope-bearing fragments, analogues or cells to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al, Immunology Today 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-pheS (beta), anti-pheS (alpha) or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

If two antigen binding domains are present each domain may be directed against a different epitope—termed 'bispecific' antibodies.

The above-described antibodies may be employed to isolate or to identify clones expressing the polypeptides to purify the polypeptides by affinity chromatography.

Thus, among others, antibodies against pheS (beta)- and/or pheS (alpha)-polypeptide may be employed to treat infections, particularly bacterial infections and especially otitis media, conjunctivitis, pneumonia, bacteremia, meningitis, sinusitis, pleural empyema and endocarditis, and most particularly meningitis, such as for example infection of cerebrospinal fluid.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized"; where the complimentarity determining region(s) of the hybridoma-derived antibody has been transplanted into a human monoclonal antibody , for example as described in Jones, P. et al. (1986), Nature 321, 522–525 or Tempest et al., (1991) Biotechnology 9, 266–273.

The use of a polynucleotide of the invention in genetic immunization will preferably employ a suitable delivery method such as direct injection of plasmid DNA into muscles (Wolff et al., Hum Mol Genet 1992, 1: 363, Manthorpe et al., Hum. Gene Ther. 1963: 4, 419), delivery of DNA complexed with specific protein carriers (Wu et al., J Biol Chem. 1989: 264,16985), coprecipitation of DNA with calcium phosphate (Benvenisty & Reshef, PNAS, 1986:

83,9551), encapsulation of DNA in various forms of liposomes (Kaneda et al., Science 1989: 243,375), particle bombardment (Tang et al., Nature 1992, 356: 152, Eisenbraun et al., DNA Cell Biol 1993, 12: 791) and in vivo infection using cloned retroviral vectors (Seeger et al., PNAS 1984: 81,5849).

Antagonists and Agonists—Assays and Molecules

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of pheS (beta) and/or pheS (alpha) polypeptides, including dimers of pheS (beta) and pheS (alpha), or polynucleotides, particularly those compounds that are bacteriostatic and/or bacteriocidal. The method of screening may involve high-throughput techniques. For example, to screen for agonists or antagonists, a synthetic reaction mix, a cellular compartment, such as a membrane, cell envelope or cell wall, or a preparation of any thereof, comprising pheS (beta) and/or pheS (alpha) polypeptide and a labeled substrate or ligand of such polypeptide is incubated in the absence or the presence of a candidate molecule that may be a pheS (beta) and/or pheS (alpha) agonist or antagonist. The ability of the candidate molecule to agonize or antagonize the pheS (beta) and/or pheS (alpha) polypeptide is reflected in decreased binding of the labeled ligand or decreased production of product from such substrate. Molecules that bind gratuitously, i.e., without inducing the effects of pheS (beta) and/or pheS (alpha) polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in pheS (beta) and/or pheS (alpha) polynucleotide or polypeptide activity, and binding assays known in the art.

Another example of an assay for pheS (beta) and/or pheS (alpha) antagonists is a competitive assay that combines pheS (beta) and/or pheS (alpha) and a potential antagonist with pheS (beta)- and/or pheS (alpha)-binding molecules, recombinant pheS (beta) and/or pheS (alpha) binding molecules, natural substrates or ligands, or substrate or ligand mimetics, under appropriate conditions for a competitive inhibition assay. pheS (beta) and pheS (alpha) can be labeled, such as by radioactivity or a colorimetric compound, such that the number of pheS (beta) and/or pheS (alpha) molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing pheS (beta)- and/or pheS (alpha) induced activities, thereby preventing the action of pheS (beta) and/or pheS (alpha) by excluding pheS (beta) and/or pheS (alpha) from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, J. Neurochem. 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of pheS (beta) and/or pheS (alpha).

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block pheS (beta) and/or pheS (alpha) protein-mediated mammalian cell invasion by, for example, initiating phosphorylation of mammalian tyrosine kinases (Rosenshine et al., *Infect. Immun.* 60: 2211 (1992); to block bacterial adhesion between mammalian extracellular matrix proteins and bacterial pheS (beta) and/or pheS (alpha) proteins that mediate tissue damage and; to block the normal progression of pathogenesis in infections initiated other than by the implantation of indwelling devices or by other surgical techniques.

The antagonists and agonists of the invention may be employed, for instance, to inhibit and treat otitis media, conjunctivitis, pneumonia, bacteremia, meningitis, sinusitis, pleural empyema and endocarditis, and most particularly meningitis, such as for example infection of cerebrospinal fluid.

Vaccines

Another aspect of the invention relates to a method for inducing an immunological response in an individual, particularly a mammal which comprises inoculating the individual with pheS (beta) and/or pheS (alpha), or a fragment or variant thereof, such as pheS (alpha)-pheS (beta) fusions, adequate to produce antibody and/or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector to direct expression of pheS (beta) and/or pheS (alpha), or a fragment, fusion or a variant thereof, for expressing pheS (beta) and/or pheS (alpha), or a fragment, fusion or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to a pheS (beta) and/or pheS (alpha) or protein coded from either, wherein the composition comprises a recombinant pheS (beta) and/or pheS (alpha) or protein coded from either comprising DNA which codes for and expresses an antigen of said pheS (beta) and/or pheS (alpha) or protein coded from either. The immunological response may be used therapeutically or prophylactically and may take the form of antibody immunity or cellular immunity such as that arising from CTL or CD4+ T cells.

A pheS (beta) or pheS (alpha) polypeptide or a fragment of either or fused fragments from both may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the coprotein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Streptococcus pneumoniae* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Streptococcus pneumoniae* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and nonaqueous sterile injection solutions which may contain anti-oxidants, buffers, bacteriostats and solutes which render the formulation insotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain pheS (beta) and pheS (alpha) protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially Streptococcus pneumoniae wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1µg/ml to 10mg/ml for bathing of wounds or indwelling devices.

A vaccine composition is conveniently in injectable form. Conventional adjuvantse may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The examples below are carried out using standard techniques, which are well known and routine to those of skill in the art, except where otherwise described in detail. The examples are illustrative, but do not limit the invention.

Example 1

Strain selection, Library Production and Sequencing

The polynucleotides having the DNA sequence given in SEQ ID NO:1 and 5 were obtained from a library of clones of chromosomal DNA of Streptococcus pneumoniae in E. coli. The sequencing data from two or more clones containing overlapping Streptococcus pneumoniae DNAs was used to construct the contiguous DNA sequence in SEQ ID NO:1 and 5. Libraries may be prepared by routine methods, for example:

Methods 1 and 2 below.

Total cellular DNA is isolated from Streptococcus pneumoniae 0100993 according to standard procedures and size-fractionated by either of two methods.

Method 1

Total cellular DNA is mechanically sheared by passage through a needle in order to size-fractionate according to standard procedures. DNA fragments of up to 11kbp in size are rendered blunt by treatment with exonuclease and DNA polymerase, and EcoRI linkers added. Fragments are ligated into the vector Lambda ZapII that has been cut with EcoRI, the library packaged by standard procedures and E. coli infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bsh1235I), and such fragments are size-fractionated according to standard procedures. EcoRI linkers are ligated to the DNA and the fragments then ligated into the vector Lambda ZapII that have been cut with EcoRI, the library packaged by standard procedures, and E. coli infected with the packaged library. The library is amplified by standard procedures.

Example 2 pheS (beta) and pheS (alpha) Characterization

The enzyme mediated incorporation of radiolabelled amino acid into tRNA may be measured by the aminoacylation method which measures amino acid-tRNA as trichloroacetic acid-precipitable radioactivity from radiolabelled amino acid in the presence of tRNA and ATP (Hughes J, Mellows G and Soughton S, 1980, FEBS Letters, 122: 322–324). Thus inhibitors of phenylalanyl tRNA synthetase heterodimer can be detected by a reduction in the trichloroacetic acid precipitable radioactivity relative to the control. Alternatively the tRNA synthetase catalysed partial PPi/ATP exchange reaction which measures the formation of radiolabelled ATP from PPi can be used to detect phenylalanyl tRNA synthetase heterodimer inhibitors (Calender R & Berg P, 1966, Biochemistry, 5, 1681–1690).

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2350 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:1:

```
ATGCTTGTAT CTTATAAATG GTTAAAAGAA TTGGTGGACA TTGATGTGCC ATCACAAGAG        60
TTGGCTGAAA AAATGTCAAC TACAGGGATC GAGGTAGAGG GTGTCGAATT ACCAGCTGCT       120
GGTCTCTCAA AAATTGTCGT CGGTGAGGTC TTGTCTTGCG AAGCTGTGCC AGAGACTCAC       180
CTCCATGTTT GTCAGATTAA CGTTGGCGAA GAAGAAGAGC GTCAGATCGT TTGTGGTGCC       240
CCAAATGTGC GTGCTGGGAT CAAGGTCATG GTGGCTCTTC AGGAGCTCG TATCGCTGAT        300
AACTACAAAA TCAAAAAAGG AAAAATCCGT GGTTTGGAGT CACTTGGAAT GATCTGTTCA       360
CTTGGTGAAT GGGAATTTC TGACTCAGTT GTGCCTAAGG AATTCGCAGA TGGCATCCAA        420
ATCTTGCCTG AAGATGCCGT GCCAGGTGAG GAAGTCTTTT CTTACCTAGA CTTGGATGAT       480
GAAATCATCG AACTTTCCAT CACACCAAAC CGTGCAGATG CCCTTTCTAT GTGTGGAGTG       540
GCTCACGAAG TGGCAGCCAT CTATGACAAG GCAGTCAACT TTAAAAAATT TACTCTAACA       600
GAAACTAATG AAGCTGCGGC AGATGCCCTT TCTGTCAGCA TTGAGACAGA CAAGGCGCCT       660
TACTATGCAG CTCGTATCTT GGACAATGTG ACTATCGCAC CAAGTCCACA ATGGTTGCAA       720
AACCTTCTCA TGAACGAAGG CATCCGTCCC ATCAATAACG TTGTAGACGT GACAAACTAC       780
ATCCTGCTCT ACTTGGTCA ACCTATGCAT GCTTTTGACT TGGACACATT TGAAGGGACT        840
GACATCCGTG TGCGTGAAGC GCGTGATGGT GAAAAATTAG TGACCCTGGA CGGTGAAGAA       900
CGAGACTTGG CTGAGACAGA CCTCGTGATT ACAGTTGCTG ACAAACCAGT AGCCCTTGCC       960
GGTGTTATGG GTGGTCAGGC TACAGAAATT TCTGAAAAAT CTAGTCGTGT TATCCTTGAA      1020
GCTGCTGTTT TTAATGGCAA ATCTATCCGT AAGACAAGTG GTCGCCTGAA CCTTCGTTCT      1080
GAGTCATCTT CTCGCTTTGA AAAAGGAATT AATGTGGCAA CAGTTAATGA AGCCCTTGAT      1140
GCGGCAGCTA GCATGATTGC AGAGCTTGCA GGCGCGACGG TGCGTAAGGG TATCGTTTCA      1200
GCGGGTGAGC TTGATACCTC TGATGTGGAA GTTTCTTCAA CCCTTGCTGA TGTTAACCGT      1260
GTCCTCGGAA CTGAGCTGTC TTATGCTGAT GTANAAGACG TCTTCCGTCG TCTTGGCTTT      1320
GGTCTTTCTG GAAATGCAGA CAGCTTTACA GTCAGCGTAC CACGTCGTCG TTGGGATATC      1380
ACAATCGAAG CTGATCTCTT TGAAGAAATC GCTCGTATCT ATGGATATGA CCGCTTGCCA      1440
ACCAGCCTTC CAAAAGACGA TGGTACAGCT GGTGAATTGA CTGTGATACA AAAACTCCGC      1500
CGTCAAGTTC GTACCATTGC TGAAGGAGCA GGTTTGACAG AAATCATCAC CTATGCTCTG      1560
ACAACTCCTG AAAAAGCAGT TGAGTTCACA GCTCAACCAA GTAACCTTAC TGAACTCATG      1620
TGGCCAATGA CTGTGGATCG TTCAGTCCTC CGTCAAAATA TGATTTCAGG GATCCTTGTT      1680
ACCGTTGCCT ACAACGTGGC TCGTAAGAAT AAAAACTTGG CCCTTTATGA GATTGGAAAA      1740
GTCTTTGAAC AAACAGGTAA TCCAAAAGAA GAACTTCCAA ATGAGATCAA CAGCTTTGCC      1800
```

| | | | | | |
|---|---|---|---|---|---|
|TTTGCTTTGA|CAGGCTTGGT|TGCTGAAANA|GATTTCCAAA|CAGCAGCAGT|TCCAGTTGAT 1860|
|TTTTTTTATG|CTAAGGGAAT|CCTTGAAGCC|NTATTTACTC|GTTTGGGACT|CCAAGTAACC 1920|
|TATACAGCAA|CATCTGAAAT|CGNTAGCCTT|CATCCAGGTC|GTACAGCCGT|GATTCACTC 1980|
|GGTGACCAAG|TTCTTGGTTT|CCTTGGCCAA|GTGCATCCAG|TCACTGCCAA|GGCTTACGAT 2040|
|ATTCCAGAAA|CGTATGTAGC|TGAGCTTAAC|CTTTCAGCCA|TCGAAGGGGC|GCTCCAACCT 2100|
|GCTGTTCCAT|TTGTGGAAAT|CACCAGATTC|CCAGCAGTCA|GCCGTGACGT|TGCCTTTCTC 2160|
|CTCAAGGCAG|AAGTGACTCA|CCAAGCAGTT|GTAGATGCTA|TCCAAGCTGC|CGGCGTGAAA 2220|
|CGTTTGACAG|ATATCAGACT|CTTTGACGTC|TTCTCAGGTG|AAAAACTGGG|ACTTGGTATG 2280|
|AAGTCAATGG|CTTATAGCTT|GACCTTCCAA|AATCCAGAAG|ACAGCTTAAC|GGACGAAGAA 2340|
|GTCGCACGCT| | | | | 2350|

( 2 ) INFORMATION FOR SEQ ID NO:2:

( i ) SEQUENCE CHARACTERISTICS:
        ( A ) LENGTH: 783 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Leu Val Ser Tyr Lys Trp Leu Lys Glu Leu Val Asp Ile Asp Val
 1               5                  10                  15

Pro Ser Gln Glu Leu Ala Glu Lys Met Ser Thr Thr Gly Ile Glu Val
            20                  25                  30

Glu Gly Val Glu Leu Pro Ala Ala Gly Leu Ser Lys Ile Val Gly
        35                  40                  45

Glu Val Leu Ser Cys Glu Ala Val Pro Glu Thr His Leu His Val Cys
 50                  55                  60

Gln Ile Asn Val Gly Glu Glu Glu Arg Gln Ile Val Cys Gly Ala
 65                  70                  75                  80

Pro Asn Val Arg Ala Gly Ile Lys Val Met Val Ala Leu Pro Gly Ala
                85                  90                  95

Arg Ile Ala Asp Asn Tyr Lys Ile Lys Lys Gly Lys Ile Arg Gly Leu
                100                 105                 110

Glu Ser Leu Gly Met Ile Cys Ser Leu Gly Glu Leu Gly Ile Ser Asp
            115                 120                 125

Ser Val Val Pro Lys Glu Phe Ala Asp Gly Ile Gln Ile Leu Pro Glu
    130                 135                 140

Asp Ala Val Pro Gly Glu Val Phe Ser Tyr Leu Asp Leu Asp
145                 150                 155                 160

Glu Ile Ile Glu Leu Ser Ile Thr Pro Asn Arg Ala Asp Ala Leu Ser
                165                 170                 175

Met Cys Gly Val Ala His Glu Val Ala Ala Ile Tyr Asp Lys Ala Val
            180                 185                 190

Asn Phe Lys Lys Phe Thr Leu Thr Glu Thr Asn Glu Ala Ala Ala Asp
        195                 200                 205

Ala Leu Ser Val Ser Ile Glu Thr Asp Lys Ala Pro Tyr Tyr Ala Ala
    210                 215                 220

Arg Ile Leu Asp Asn Val Thr Ile Ala Pro Ser Pro Gln Trp Leu Gln
225                 230                 235                 240

Asn Leu Leu Met Asn Glu Gly Ile Arg Pro Ile Asn Asn Val Val Asp
                245                 250                 255
```

| | | | | | | | | | | | | | | |
|---|---|---|---|---|---|---|---|---|---|---|---|---|---|---|
|Val|Thr|Asn|Tyr 260|Ile|Leu|Leu|Tyr|Phe 265|Gly|Gln|Pro|Met|His 270|Ala|Phe|
|Asp|Leu|Asp 275|Thr|Phe|Glu|Gly|Thr 280|Asp|Ile|Arg|Val|Arg 285|Glu|Ala|Arg|
|Asp|Gly 290|Glu|Lys|Leu|Val|Thr 295|Leu|Asp|Gly|Glu|Arg 300|Asp|Leu|Ala|
|Glu 305|Thr|Asp|Leu|Val|Ile 310|Thr|Val|Ala|Asp|Lys 315|Pro|Val|Ala|Leu|Ala 320|
|Gly|Val|Met|Gly|Gly 325|Gln|Ala|Thr|Glu|Ile 330|Ser|Glu|Lys|Ser|Ser 335|Arg|
|Val|Ile|Leu|Glu 340|Ala|Ala|Val|Phe|Asn 345|Gly|Lys|Ser|Ile|Arg 350|Lys|Thr|
|Ser|Gly|Arg 355|Leu|Asn|Leu|Arg|Ser 360|Glu|Ser|Ser|Arg|Phe 365|Glu|Lys|
|Gly|Ile|Asn 370|Val|Ala|Thr|Val 375|Asn|Glu|Ala|Leu|Asp 380|Ala|Ala|Ala|Ser|
|Met 385|Ile|Ala|Glu|Leu|Ala 390|Gly|Ala|Thr|Val|Arg 395|Lys|Gly|Ile|Val|Ser 400|
|Ala|Gly|Glu|Leu|Asp 405|Thr|Ser|Asp|Val|Glu 410|Val|Ser|Ser|Thr|Leu 415|Ala|
|Asp|Val|Asn|Arg 420|Val|Leu|Gly|Thr|Glu 425|Leu|Ser|Tyr|Ala|Asp 430|Val|Xaa|
|Asp|Val|Phe 435|Arg|Arg|Leu|Gly|Phe 440|Gly|Leu|Ser|Gly|Asn 445|Ala|Asp|Ser|
|Phe|Thr 450|Val|Ser|Val|Pro|Arg 455|Arg|Arg|Trp|Asp|Ile 460|Thr|Ile|Glu|Ala|
|Asp 465|Leu|Phe|Glu|Glu|Ile 470|Ala|Arg|Ile|Tyr|Gly 475|Tyr|Asp|Arg|Leu|Pro 480|
|Thr|Ser|Leu|Pro|Lys 485|Asp|Asp|Gly|Thr|Ala 490|Gly|Glu|Leu|Thr|Val 495|Ile|
|Gln|Lys|Leu|Arg 500|Arg|Gln|Val|Arg|Thr 505|Ile|Ala|Glu|Gly|Ala 510|Gly|Leu|
|Thr|Glu|Ile 515|Ile|Thr|Tyr|Ala|Leu 520|Thr|Thr|Pro|Glu|Lys 525|Ala|Val|Glu|
|Phe|Thr 530|Ala|Gln|Pro|Ser|Asn 535|Leu|Thr|Glu|Leu|Met 540|Trp|Pro|Met|Thr|
|Val 545|Asp|Arg|Ser|Val|Leu 550|Arg|Gln|Asn|Met|Ile 555|Ser|Gly|Ile|Leu|Val 560|
|Thr|Val|Ala|Tyr|Asn 565|Val|Ala|Arg|Lys|Asn 570|Lys|Asn|Leu|Ala|Leu 575|Tyr|
|Glu|Ile|Gly|Lys 580|Val|Phe|Glu|Gln|Thr 585|Gly|Asn|Pro|Lys|Glu 590|Glu|Leu|
|Pro|Asn|Glu 595|Ile|Asn|Ser|Phe|Ala 600|Phe|Ala|Leu|Thr|Gly 605|Leu|Val|Ala|
|Glu|Xaa 610|Asp|Phe|Gln|Thr|Ala 615|Ala|Val|Pro|Val|Asp 620|Phe|Phe|Tyr|Ala|
|Lys 625|Gly|Ile|Leu|Glu|Ala 630|Xaa|Phe|Thr|Arg|Leu 635|Gly|Leu|Gln|Val|Thr 640|
|Tyr|Thr|Ala|Thr|Ser 645|Glu|Ile|Xaa|Ser|Leu 650|His|Pro|Gly|Arg|Thr 655|Ala|
|Val|Ile|Ser|Leu 660|Gly|Asp|Gln|Val|Leu 665|Gly|Phe|Leu|Gly|Gln 670|Val|His|
|Pro|Val|Thr|Ala|Lys|Ala|Tyr|Asp|Ile|Pro|Glu|Thr|Tyr|Val|Ala|Glu|

|   |   |   |   |   |   | 675 |   |   |   |   |   | 680 |   |   |   |   |   | 685 |   |   |
|---|---|---|---|---|---|---|---|---|---|---|---|---|---|---|---|---|---|---|---|---|

Leu Asn Leu Ser Ala Ile Glu Gly Ala Leu Gln Pro Ala Val Pro Phe
     690               695              700

Val Glu Ile Thr Arg Phe Pro Ala Val Ser Arg Asp Val Ala Phe Leu
705              710            715              720

Leu Lys Ala Glu Val Thr His Gln Ala Val Val Asp Ala Ile Gln Ala
              725              730          735

Ala Gly Val Lys Arg Leu Thr Asp Ile Arg Leu Phe Asp Val Phe Ser
         740               745              750

Gly Glu Lys Leu Gly Leu Gly Met Lys Ser Met Ala Tyr Ser Leu Thr
     755               760            765

Phe Gln Asn Pro Glu Asp Ser Leu Thr Asp Glu Glu Val Ala Arg
770              775            780

( 2 ) INFORMATION FOR SEQ ID NO:3:

( i ) SEQUENCE CHARACTERISTICS:
       ( A ) LENGTH: 455 base pairs
       ( B ) TYPE: nucleic acid
       ( C ) STRANDEDNESS: single
       ( D ) TOPOLOGY: linear ( i i ) MOLECULE TYPE: Genomic DNA ( x i ) SEQUENCE DESCRIPTION: SEQ ID NO:3:

```
CGTATCGCTG ATAACTACAA AATCAAAAAA GGAAAAATCC GTGGTTTGGA GTCACTTGGA      60
ATGATCTGTT CACTTGGTGA ATTGGGAATT TCTGACTCAG TTGTGCCTAA GGAATTCGCA     120
GATGGCATCC AAATCTTGCC TGAAGATGCC GTGCCAGGTG AGGAAGTCTT TTCTTACCTA     180
GACTTGGATG ATGAAATCAT CGAACTTTCC ATCACACCAA ACCGTGCAGA TGCCCTTTCT     240
ATGTGTGGAG TGGCTCACGA AGTGGCAGCC ATCTATGACA AGGCAGTCAA CTTTAAAAAA     300
TTACTCTAA CAGAAACTAA TGAAGCTGCG GCAGATGCCC TTTCTGTCAG CATTGAGACA      360
GACAAGGCGC CTTACTATGC AGCTCGTATC TTGGACAATG TGACTATCGC ACCAAGTCCA     420
CAATGGTTGC AAAACCTTCT CATGAACGAA GCATC                                455
```

( 2 ) INFORMATION FOR SEQ ID NO:4:

( i ) SEQUENCE CHARACTERISTICS:
       ( A ) LENGTH: 151 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:4:

Arg Ile Ala Asp Asn Tyr Lys Ile Lys Lys Gly Lys Ile Arg Gly Leu
1              5                10             15

Glu Ser Leu Gly Met Ile Cys Ser Leu Gly Glu Leu Gly Ile Ser Asp
         20               25              30

Ser Val Val Pro Lys Glu Phe Ala Asp Gly Ile Gln Ile Leu Pro Glu
           35             40             45

Asp Ala Val Pro Gly Glu Glu Val Phe Ser Tyr Leu Asp Leu Asp Asp
     50               55            60

Glu Ile Ile Glu Leu Ser Ile Thr Pro Asn Arg Ala Asp Ala Leu Ser
65              70             75          80

Met Cys Gly Val Ala His Glu Val Ala Ala Ile Tyr Asp Lys Ala Val
             85             90             95

| Asn | Phe | Lys | Lys | Phe | Thr | Leu | Thr | Glu | Thr | Asn | Glu | Ala | Ala | Ala | Asp |
|-----|-----|-----|-----|-----|-----|-----|-----|-----|-----|-----|-----|-----|-----|-----|-----|
|     |     |     | 100 |     |     |     |     | 105 |     |     |     | 110 |     |     |     |

| Ala | Leu | Ser | Val | Ser | Ile | Glu | Thr | Asp | Lys | Ala | Pro | Tyr | Tyr | Ala | Ala |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Arg | Ile | Leu | Asp | Asn | Val | Thr | Ile | Ala | Pro | Ser | Pro | Gln | Trp | Leu | Gln |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Asn | Leu | Leu | Met | Asn | Glu | Ala |
|-----|-----|-----|-----|-----|-----|-----|
| 145 |     |     |     |     | 150 |     |

( 2 ) INFORMATION FOR SEQ ID NO:5:

( i ) SEQUENCE CHARACTERISTICS:
        ( A ) LENGTH: 1047 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:5:

```
GGATCCCCCG  GGCTGCAGGA  ATTAAAAGCG  CTTCGCGAAG  AAACGCTGAC  TAGCTTGAAG     60
CAGATTACTG  CTGGAAATGA  AAAAGAGATG  CAAGATTTGC  GTGTCTCTGT  CCTTGGTAAA    120
AAGGGTTCGC  TTACTGAAAT  CCTCAAAGGG  ATGAAAGATG  TTTCTGCTGA  GATGCGTCCA    180
ATCATCGGGA  ACACGTCAA   TGAAGCTCGT  GATGTCTTGA  CAGCTGCTTT  TGAAGAAACA    240
GCTAAGCTCT  TGGAAGAAAA  GAAAGTCGCG  GCTCAACTGG  CTAGCGAGAG  TATCGATGTG    300
ACGCTTCCAG  GTCGTCCAGT  TGCGACTGGT  CACCGTCACG  TTTTGACACA  AACCAGTGAA    360
GAAATCGAAG  ATATCTTCAT  CGGTATGGGT  TATCAAGTCG  TGGATGGTTT  TGAAGTGGAG    420
CAAGACTACT  ATAACTTTGA  ACGTATGAAC  CTTCCAAAAG  ACCACCCAGC  TCGTGATATG    480
CAGGATACTT  TCTATATCAC  TGAAGAAATC  TTGCTCCGTA  CCCACACGTC  TCCAGTTCAG    540
GCACGTGCTA  TGGATGCCCA  TGATTTTCT   AAAGGTCCTT  TGAAGATAAT  CTCGCCAGGG    600
CGTGTCTTCC  GTCGCGATAC  GGACGATGCG  ACCCACAGTC  ACCAATTCCA  CCAAATCGAA    660
GGCTTGGTAG  TTGGGAAAAA  TATCTCTATG  GCTGATCTTC  AAGGAACGCT  TCAGTTGATT    720
GTCCAAAAAA  TGTTTGGTGA  AGAGCGTCAA  ATTCGTTTGC  GTCCATCTTA  CTTCCCATTC    780
ACAGAGCCAT  CTGTTGAGGT  GGATGTTTCT  TGCTTCAAAT  GTGGTGGAGA  AGGCTGTAAC    840
GTATGTAAGA  AAACAGGTTG  GATCGAAATT  ATGGGGGCCG  GTATGGTTCA  CCCACGTGTC    900
CTTGAAATGA  GTGGTATCGA  TGCGACTGTA  TACTCTGGCT  TTGCCTTTGG  TCTTGGACAA    960
GAGCGTGTAG  CTATGCTCCG  TTATGGAATC  AACGATATCC  GTGGATTCTA  CCAAGGAGAT   1020
GTCCGCTTCT  CAGAACAGTT  TAAATAA                                         1047
```

( 2 ) INFORMATION FOR SEQ ID NO:6:

( i ) SEQUENCE CHARACTERISTICS:
        ( A ) LENGTH: 348 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

| Gly | Ser | Pro | Gly | Leu | Gln | Glu | Leu | Lys | Ala | Leu | Arg | Glu | Glu | Thr | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Ser | Leu | Lys | Gln | Ile | Thr | Ala | Gly | Asn | Glu | Lys | Glu | Met | Gln | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

```
Leu Arg Val Ser Val Leu Gly Lys Lys Gly Ser Leu Thr Glu Ile Leu
    35              40                  45
Lys Gly Met Lys Asp Val Ser Ala Glu Met Arg Pro Ile Ile Gly Lys
50                  55                  60
His Val Asn Glu Ala Arg Asp Val Leu Thr Ala Ala Phe Glu Glu Thr
65              70                  75                  80
Ala Lys Leu Leu Glu Glu Lys Lys Val Ala Ala Gln Leu Ala Ser Glu
                85                  90                  95
Ser Ile Asp Val Thr Leu Pro Gly Arg Pro Val Ala Thr Gly His Arg
            100                 105             110
His Val Leu Thr Gln Thr Ser Glu Glu Ile Glu Asp Ile Phe Ile Gly
        115                 120                 125
Met Gly Tyr Gln Val Val Asp Gly Phe Glu Val Glu Gln Asp Tyr Tyr
130                 135                 140
Asn Phe Glu Arg Met Asn Leu Pro Lys Asp His Pro Ala Arg Asp Met
145                 150                 155                 160
Gln Asp Thr Phe Tyr Ile Thr Glu Glu Ile Leu Leu Arg Thr His Thr
                165                 170                 175
Ser Pro Val Gln Ala Arg Ala Met Asp Ala His Asp Phe Ser Lys Gly
            180                 185                 190
Pro Leu Lys Ile Ile Ser Pro Gly Arg Val Phe Arg Arg Asp Thr Asp
        195                 200                 205
Asp Ala Thr His Ser His Gln Phe His Gln Ile Glu Gly Leu Val Val
210                 215                 220
Gly Lys Asn Ile Ser Met Ala Asp Leu Gln Gly Thr Leu Gln Leu Ile
225                 230                 235                 240
Val Gln Lys Met Phe Gly Glu Glu Arg Gln Ile Arg Leu Arg Pro Ser
                245                 250                 255
Tyr Phe Pro Phe Thr Glu Pro Ser Val Glu Val Asp Val Ser Cys Phe
            260                 265                 270
Lys Cys Gly Gly Glu Gly Cys Asn Val Cys Lys Lys Thr Gly Trp Ile
        275                 280                 285
Glu Ile Met Gly Ala Gly Met Val His Pro Arg Val Leu Glu Met Ser
290                 295                 300
Gly Ile Asp Ala Thr Val Tyr Ser Gly Phe Ala Phe Gly Leu Gly Gln
305                 310                 315                 320
Glu Arg Val Ala Met Leu Arg Tyr Gly Ile Asn Asp Ile Arg Gly Phe
                325                 330                 335
Tyr Gln Gly Asp Val Arg Phe Ser Glu Gln Phe Lys
            340                 345
```

( 2 ) INFORMATION FOR SEQ ID NO:7:

( i ) SEQUENCE CHARACTERISTICS:
        ( A ) LENGTH: 197 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:7:

```
CAATTCCACC AAATCGAAGG CTTGGTAGTT GGGAAAAATA TCTCTATGGC TGATCTTCAA      60
GGAACGCTTC AGTTGATTGT CCAAAAAATG TCTGGTGAAG AGCGTCAAAT TCGTTTGCGT     120
CCATCTTACT TCCCATTCAC ACACCCATCT GTTGAGGTGG ATGTTTCTTG CTTCAAATGT     180
GGTGGAGAAG GCTGTAA                                                   197
```

(2) INFORMATION FOR SEQ ID NO:8:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Gln Phe His Gln Ile Glu Gly Leu Val Val Gly Lys Asn Ile Ser Met
 1               5                  10                  15
Ala Asp Leu Gln Gly Thr Leu Gln Leu Ile Val Gln Lys Met Ser Gly
            20                  25                  30
Glu Glu Arg Gln Ile Arg Leu Arg Pro Ser Tyr Phe Pro Phe Thr His
        35                  40                  45
Pro Ser Val Glu Val Asp Val Ser Cys Phe Lys Cys Gly Gly Glu Gly
    50                  55                  60
Cys
65
``` what is claimed is:

1. An isolated polynucleotide comprising a polynucleotide sequence selected from the group consisting of:

(a) a polynucleotide having at least a 95% identity to a polynucleotide encoding a polypeptide comprising the amino acid sequence of the reference sequence of SEQ ID NO:2;

(b) a polynucleotide having at least a 97% identity to a polynucleotide encoding a polypeptide comprising the amino acid sequence of the reference sequence of SEQ ID NO:2;

(c) a polynucleotide encoding a polypeptide comprising the amino acid sequence of the reference sequence of SEQ ID NO:2;

(d) a polynucleotide hybridizing under stringent conditions to a polynucleotide encoding a polypeptide comprising the amino acid sequence of the reference sequence of SEQ ID NO:2;

(e) a polynucleotide having at least a 95% identity to a polynucleotide encoding the same mature polypeptide expressed by the phenylalanyl tRNA synthetase beta subunit gene contained in NCIMB Deposit No. 40794;

(f) a polynucleotide having at least a 97% identity to a polynucleotide encoding the same mature polypeptide expressed by the phenylalanyl tRNA synthetase beta subunit gene contained in NCIMB Deposit No. 40794;

(g) a polynucleotide encoding the same mature polypeptide expressed by the phenylalanyl tRNA synthetase beta subunit gene contained in NCIMB Deposit No. 40794;

(i) a polynucleotide which is complementary to the polynucleotide of (a), (b), (c), (d), (e), (f) or (g).

2. The isolated polynucleotide of claim 1 wherein said polynucleotide is a polynucleotide having at least a 95% identity to a polynucleotide encoding a polypeptide comprising the amino acid sequence of the reference sequence of SEQ ID NO:2.

3. The isolated polynucleotide of claim 1 wherein said polynucleotide is a polynucleotide having at least a 97% identity to a polynucleotide encoding a polypeptide comprising the amino acid sequence of the reference sequence of SEQ ID NO:2.

4. The isolated polynucleotide of claim 1 wherein said polynucleotide is a polynucleotide encoding a polypeptide comprising the amino acid sequence of the reference sequence of SEQ ID NO:2.

5. The isolated polynucleotide of claim 1 wherein said polynucleotide is a polynucleotide hybridizing under stringent conditions to a polynucleotide encoding a polypeptide comprising the amino acid sequence of the reference sequence of SEQ ID NO:2.

6. The isolated polynucleotide of claim 1 wherein said polynucleotide is a polynucleotide having at least a 95% identity to a polynucleotide encoding the same mature polypeptide expressed by the phenylalanyl tRNA synthetase beta subunit gene contained in NCIMB Deposit No. 40794.

7. The isolated polynucleotide of claim 1 wherein said polynucleotide is a polynucleotide having at least a 97% identity to a polynucleotide encoding the same mature polypeptide expressed by the phenylalanyl tRNA synthetase beta subunit gene contained in NCIMB Deposit No. 40794.

8. The isolated polynucleotide of claim 1 wherein said polynucleotide is a polynucleotide encoding the same mature polypeptide expressed by the phenylalanyl tRNA. synthetase beta subunit gene contained in NCIMB Deposit No. 40794.

9. The polynucleotide of claim 1 wherein the polynucleotide is DNA.

10. The polynucleotide of claim 1 wherein the polynucleotide is RNA.

11. The polynucleotide of claim 4 wherein the polynucleotide is DNA.

12. The polynucleotide of claim 4 wherein the polynucleotide is RNA.

13. The polynucleotide of claim 4 comprising the nucleotides 1 to 2350 set forth in SEQ ID NO:1.

14. The polynucleotide of claim 4 which encodes a polypeptide consisting of amino acid 1 to 783 of SEQ ID NO:2.

15. A vector comprising the DNA of claim 11.

16. A host cell comprising the vector of claim 15.

17. A process for producing a polypeptide comprising: expressing from the host cell of claim 16 a polypeptide encoded by said DNA.

18. A process for producing a cell which expresses a polypeptide comprising transforming or transfecting the cell with the vector of claim 15 such that the cell expresses the polypeptide encoded by the DNA contained in the vector.

19. A process for producing a cell which expresses a polypeptide conspiring transforming or transfecting the cell with the vector of claim 15 such that the cell expresses the polypeptide encoded by the DNA contained in the vector.

20. A process for producing a tRNA synthetase polypeptide or fragment, which fragment retains binding and/or catalytic activity, comprising culturing a host of claim 16 under conditions sufficient for the production of said polypeptide or fragment.

21. An isolated polynucleotide comprising the polynucleotide sequence set forth in SEQ ID NO:1.

22. An isolated polynucleotide comprising the nucleotides 1 to 2350 set forth in SEQ ID NO:1.

23. An isolated polynucleotide comprising the polynucleotide sequence set forth in SEQ ID NO:1, 3, 5 or 7.

24. An isolated polynucleotide consisting of the polynucleotide sequence set forth in SEQ ID NO:1, 3, 5 or 7.

25. An isolated polynucleotide comprising a DNA sequence obtained by screening an appropriate library containing the complete gene encoding an amino acid sequence set forth in SEQ ID NO:2 under stringent hybridization conditions with a probe having a polynucleotide sequence encoding the amino acid sequence set forth in SEQ ID NO:2 or a fragment thereof, which fragment retains binding and/or catalytic activity; and isolating said DNA sequence.

26. The isolated polynucleotide of claim 25 comprising of nucleotides 1 to 2350 set forth in SEQ ID NO:1.

27. An isolated polynucleotide comprising a polynucleotide sequence selected from the group consisting of:
(a) a polynucleotide having at least a 95% identity to a polynucleotide encoding a polypeptide comprising the amino acid sequence of the reference sequence of SEQ ID NO:6;
(b) a polynucleotide having at least a 97% identity to a polynucleotide encoding a polypeptide comprising the amino acid sequence of the reference sequence of SEQ ID NO:6;
(c) a polynucleotide encoding a polypeptide comprising the amino acid sequence of the reference sequence of SEQ ID NO:6;
(d) a polynucleotide hybridizing under stringent conditions to a polynucleotide encoding a polypeptide comprising the amino acid sequence of the reference sequence of SEQ ID NO:6;
(e) a polynucleotide having at least a 95% identity to a polynucleotide encoding the same mature polypeptide expressed by the phenylalanyl tRNA synthetase alpha subunit gene contained in NCIMB Deposit No. 40794;
(f) a polynucleotide having at least a 97% identity to a polynucleotide encoding the same mature polypeptide expressed by the phenylalanyl tRNA synthetase alpha subunit gene contained in NCIMB Deposit No. 40794;
(g) a polynucleotide encoding the same mature polypeptide expressed by the phenylalanyl tRNA synthetase alpha subunit gene contained in NCIMB Deposit No. 40794;
(i) a polynucleotide which is complementary to the polynucleotide of (a), (b), (c), (d), (e), (f) or (g).

28. The isolated polynucleotide of claim 27 wherein said polynucleotide is a polynucleotide having at least a 95% identity to a polynucleotide encoding a polypeptide comprising the amino acid sequence of the reference sequence of SEQ ID NO:6.

29. The isolated polynucleotide of claim 27 wherein said polynucleotide is a polynucleotide having at least a 97% identity to a polynucleotide encoding a polypeptide comprising the amino acid sequence of the reference sequence of SEQ ID NO:6.

30. The isolated polynucleotide of claim 27 wherein said polynucleotide is a polynucleotide encoding a polypeptide comprising the amino acid sequence of the reference sequence of SEQ ID NO:6.

31. The isolated polynucleotide of claim 27 wherein said polynucleotide is a polynucleotide hybridizing under stringent conditions to a polynucleotide encoding a polypeptide comprising the amino acid sequence of the reference sequence of SEQ ID NO:6.

32. The isolated polynucleotide of claim 27 wherein said polynucleotide is a polynucleotide having at least a 95% identity to a polynucleotide encoding the same mature polypeptide expressed by the phenylalanyl tRNA synthetase alpha subunit gene contained in NCIMB Deposit No. 40794.

33. The isolated polynucleotide of claim 27 wherein said polynucleotide is a polynucleotide having at least a 97% identity to a polynucleotide encoding the same mature polypeptide expressed by the phenylalanyl tRNA synthetase alpha subunit gene contained in NCIMB Deposit No. 40794.

34. The isolated polynucleotide of claim 27 wherein said polynucleotide is a polynucleotide encoding the same mature polypeptide expressed by the phenylalanyl tRNA synthetase alpha subunit gene contained in NCIMB Deposit No. 40794.

35. The polynucleotide of claim 27 wherein the polynucleotide is DNA.

36. The polynucleotide of claim 27 wherein the polynucleotide is RNA.

37. The polynucleotide of claim 30 wherein the polynucleotide is DNA.

38. The polynucleotide of claim 30 wherein the polynucleotide is RNA.

39. The polynucleotide of claim 30 comprising the nucleotides 1 to 1044 set forth in SEQ ID NO:5.

40. The polynucleotide of claim 30 which encodes a polypeptide consisting of amino acid 1 to 348 of SEQ ID NO:6.

41. A vector comprising the DNA of claim 37.

42. A host cell comprising the vector of claim 41.

43. A process for producing a polypeptide comprising the step of: expressing from the host cell of claim 42 a polypeptide encoded by said DNA.

44. A process for producing a cell which expresses a polypeptide comprising the step of transforming or transfecting the cell with the vector of claim 15 such that the cell expresses the polypeptide encoded by the DNA contained in the vector.

45. A process for producing a cell which expresses a polypeptide comprising transforming or transfecting the cell with the vector of claim 41 such that the cell expresses the polypeptide encoded by the DNA contained in the vector.

46. A process for producing a tRNA synthetase polypeptide or fragment, which fragment retains binding and/or catalytic activity, comprising culturing a host of claim 42 under conditions sufficient for the production of said polypeptide or fragment.

47. An isolated polynucleotide comprising the polynucleotide sequence set forth in SEQ ID NO:5.

48. An isolated polynucleotide comprising the nucleotides 1 to 1044 set forth in SEQ ID NO:5.

49. An isolated polynucleotide comprising a DNA sequence obtained by screening an appropriate library containing the complete gene encoding an amino acid sequence set forth in SEQ ID NO:6 under stringent hybridization conditions with a probe having a polynucleotide sequence encoding the amino acid sequence set forth in SEQ ID NO:6 or a fragment thereof, which fragment retains binding and/or catalytic activity; and isolating said DNA sequence.

50. The isolated polynucleotide of claim 49 comprising nucleotides 1 to 1044 set forth in SEQ ID NO:5.

51. The polynucleotide of claim 1 wherein said polynucleotide sequence consists of the structure of:

```
X—(R₁)ₙ-1  ATGCTTGTAT  CTTATAAATG  GTTAAAAGAA  TTGGTGGACA  TTGATGTGCC
       51  ATCACAAGAG  TTGGCTGAAA  AAATGTCAAC  TACAGGGATC  GAGGGTAGAGG
      101  GTGTCGAATT  ACCAGCTGCT  GGTCTCTCAA  AAATTGTCGT  CGGTGAGGTC
      151  TTGTCTTGCG  AAGCTGTGCC  AGAGACTCAC  CTCCATGTTT  GTCAGATTAA
      201  CGTTGGCGAA  GAAGAAGAGC  GTCAGATCGT  TTGTGGTGCC  CCAAATGTGC
      251  GTGCTGGGAT  CAAGGTCATG  GTGGCTCTTC  CAGGAGCTCG  TATCGCTGAT
      301  AACTACAAAA  TCAAAAAAGC  AAAAATCCGT  GGTTTGGACT  CACTTGGAAT
      351  GATCTGTTCA  CTTGGTGAAT  TGGGAATTTC  TGACTCAGTT  GTGCCTAAGG
      401  AATTCGCAGA  TGGCATCCAA  ATCTTGCCTG  AAGATGCCGT  GCCAGGTGAG
      451  GAAGTCTTTT  CTTACCTAGA  CTTGGATGAT  GAAATCATCG  AACTTTCCAT
      501  CACACCAAAC  CGTGCAGATC  CCCTTTCTAT  GTGTGGAGTG  GCTCACGAAG
      551  TGGCAGCCAT  CTATGACAAG  GCAGTCAACT  TTAAAAAATT  TACTCTAACA
      601  GAAACTAATG  AAGCTGCGGC  AGATGCCCTT  TCTGTCACCA  TTGAGACAGA
      651  CAAGGCGCCT  TACTATGCAG  CTCGTATCTT  GGACAATGTG  ACTATCGCAC
      701  CAAGTCCACA  ATGGTTGCAA  AACCTTCTCA  TGAACGAAGG  CATCCGTCCC
      751  ATCAATAACG  TTGTAGACGT  GACAAACTAC  ATCCTGCTCT  ACTTTGGTCA
      801  ACCTATGCAT  GCTTTTGACT  TGGACACATT  TGAAGGGACT  GACATCCGTG
      851  TGCGTGAAGC  GCGTGATGGT  GAAAAATTAG  TGACCCTGGA  CGGTGAAGAA
      901  CGAGACTTGG  CTGACACAGA  CCTCGTGATT  ACAGTTGCTG  ACAAACCAGT
      951  AGCCCTTGCC  GGTGTTATGG  GTGGTCAGGC  TACAGAAATT  TCTGAAAAAT
     1001  CTAGTCGTGT  TATCCTTGAA  GCTGCTGTTT  TTAATGGCAA  ATCTATCCGT
     1051  AAGACAAGTG  GTCGCCTGAA  CCTTCGTTCT  GAGTCATCTT  CTCGCTTTGA
     1101  AAAAGGAATT  AATGTGGCAA  CAGTTAATGA  AGCCCTTGAT  GCGGCAGCTA
     1151  GCATGATTGC  AGAGCTTGCA  GGCGCGACGG  TGCGTAAGGG  TATCGTTTCA
     1201  GCGGGTGAGC  TTGATACCTC  TGATGTGGAA  GTTTCTTCAA  CCCTTGCTGA
     1251  TGTTAACCGT  GTCCTCGGAA  CTGACCTGTC  TTATGCTGAT  GTANAAGACG
     1301  TCTTCCGTCG  TCTTGGCTTT  GGTCTTTCTG  GAAATGCAGA  CAGCTTTACA
     1351  GTCAGCGTAC  CACCTCGTCG  TTGGGATATC  ACAATCGAAG  CTGATCTCTT
     1401  TGAAGAAATC  GCTCGTATCT  ATGGATATGA  CCGCTTGCCA  ACCAGCCTTC
     1451  CAAAAGACGA  TGGTACAGCT  GGTGAATTGA  CTGTGATACA  AAAACTCCGC
     1501  CGTCAAGTTC  GTACCATTGC  TGAAGGAGCA  GGTTTGACAG  AAATCATCAC
     1551  CTATGCTCTG  ACAACTCCTG  AAAAAGCAGT  TGAGTTCACA  GCTCAACCAA
     1601  GTAACCTTAC  TGAACTCATG  TGGCCAATGA  CTGTGGATCG  TTCAGTCCTC
     1651  CGTCAAAATA  TGATTTCAGG  GATCCTTGTT  ACCGTTGCCT  ACAACGTGGC
     1701  TCGTAAGAAT  AAAAACTTGG  CCCTTTATGA  GATTGGAAAA  GTCTTTGAAC
     1751  AAACAGGTAA  TCCAAAAGAA  GAACTTCCAA  ATGAGATCAA  CAGCTTTGCC
     1801  TTTGCTTTGA  CAGGCTTGGT  TGCTGAAANA  GATTTCCAAA  CAGCAGCAGT
     1851  TCCAGTTGAT  TTTTTTTATG  CTAAGGGAAT  CCTTGAAGCC  NTATTTACTC
     1901  GTTTGGGACT  CCAAGTAACC  TATACAGCAA  CATCTGAAAT  CGNTAGCCTT
     1951  CATCCAGGTC  GTACAGCCCT  GATTTCACTC  GGTGACCAAG  TTCTTGGTTT
     2001  CCTTGGCCAA  GTGCATCCAC  TCACTGCCAA  GGCTTACGAT  ATTCCAGAAA
     2051  CGTATGTAGC  TGAGCTTAAC  CTTTCAGCCA  TCGAAGGGGC  GCTCCAACCT
     2101  GCTGTTCCAT  TTGTGGAAAT  CACCAGATTC  CCAGCAGTCA  GCCGTGACGT
     2151  TGCCTTTCTC  CTCAAGGCAG  AAGTGACTCA  CCAAGCAGTT  GTAGATGCTA
     2201  TCCAAGCTGC  CGGCGTGAAA  CGTTTGACAG  ATATCAGACT  CTTTGACGTC
     2251  TTCTCAGGTG  AAAAACTGGG  ACTTGGTATG  AAGTCAATGG  CTTATAGCTT
     2301  GACCTTCCAA  AATCCAGAAG  ACAGCTTAAC  GGACGAAGAA  GTCGCACGCT
—(R₂)ₙ—Y
``` wherein, at the 5' end of the molecule, X is hydrogen, and at the 3' end of the molecule, Y is hydrogen or a metal. R₁ and R₂ is any nucleic acid residue, and n is an integer between 1 and 1000.

52. The polynucleotide of claim 27 wherein said polynucleotide sequence consists of the structure of:

```
X—(R₁)ₙ-1  GGATCCCCCG  GGCTGCAGGA  ATTAAAAGCG  CTTCGCGAAG  AAACGCTGAC
       51  TAGCTTGAAG  CAGATTACTG  CTGGAAATGA  AAAAGAGATG  CAAGATTTGC
      101  GTGTCTCTGT  CCTTGGTAAA  AAGGGTTCGC  TTACTGAAAT  CCTCAAAGGG
      151  ATGAAAGATG  TTTCTGCTGA  GATGCGTCCA  ATCATCGGGA  AACACGTCAA
      201  TGAAGCTCGT  GATGTCTTGA  CAGCTGCTTT  TGAAGAAACA  GCTAAGCTCT
      251  TGGAAGAAAA  GAAAGTCGCG  GCTCAACTGG  CTAGCGAGAG  TATCGATGTG
      301  ACGCTTCCAG  GTCGTCCAGT  TGCGACTGGT  CACCGTCACG  TTTTGACACA
      351  AACCAGTGAA  GAAATCGAAG  ATATCTTCAT  CGGTATGGGT  TATCAAGTCG
      401  TGGATGGTTT  TGAAGTGGAG  CAAGACTACT  ATAACTTTGA  ACGTATGAAC
      451  CTTCCAAAAG  ACCACCCAGC  TCGTGATATG  CAGGATACTT  TCTATATCAC
      501  TGAAGAAATC  TTGCTCCGTA  CCCACACGTC  TCCAGTTCAG  GCACGTGCTA
      551  TGGATGCCCA  TGATTTTTCT  AAAGGTCCTT  TGAAGATATT  CTCGCCAGGG
      601  CGTGTCTTCC  GTCGCGATAC  GGACGATGCG  ACCCACAGTC  ACCAATTCCA
      651  CCAAATCGAA  GGCTTGGTAG  TTGGGAAAAA  TATCTCTATG  GCTGATCTTC
      701  AAGGAACGCT  TCAGTTGATT  GTCCAAAAAA  TGTTTGGTGA  AGAGCGTCAA
      751  ATTCGTTTGC  GTCCATCTTA  CTTCCCATTC  ACAGAGCCAT  CTGTTGAGGT
      801  GGATGTTTCT  TGCTTCAAAT  GTGGTGGAGA  AGGCTGTAAC  GTATGTAAGA
      851  AAACAGGTTG  GATCGAAATT  ATGGGGGCCG  GTATGGTTCA  CCCACGTGTC
```

| | | | | |
|---|---|---|---|---|
| 901 CTTGAAATGA | GTGGTATCGA | TGCGACTGTA | TACTCTGGCT | TTGCCTTTGG |
| 951 TCTTGGACAA | CAGCGTGTAG | CTATGCTCCG | TTATGGAATC | AACGATATCC |
| 1001 GTGGATTCTA | CCAAGGAGAT | GTCCGCTTCT | CAGAACAGTT | TAAATAA |

—(R$_2$)$_n$—Y wherein, at the 5' end of the molecule, X is hydrogen, and at the 3' end of the molecule, Y is hydrogen or a metal, R$_1$ and R$_2$ is any nucleic acid residue, and n is an integer between 1 and 1000.

53. An isolated polynucleotide consisting of the polynucleotide sequence encoding polypeptide sequence set forth in SEQ ID NO:2, 4, 6 or 8.

* * * * *